(12) United States Patent
Hayashi et al.

(10) Patent No.: US 8,647,999 B2
(45) Date of Patent: Feb. 11, 2014

(54) METHOD FOR REGENERATING A CATALYST CONTAINING A CHA ZEOLITE

(75) Inventors: Mikio Hayashi, Kanagawa (JP); Masahiro Hara, Kanagawa (JP); Masashi Yamaguchi, Kanagawa (JP); Yumiko Yoshikawa, Kanagawa (JP); Takahiko Takewaki, Kanagawa (JP); Tohru Setoyama, Kanagawa (JP); Naoyuki Sakamoto, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 13/370,778

(22) Filed: Feb. 10, 2012

(65) Prior Publication Data

US 2012/0203048 A1 Aug. 9, 2012

Related U.S. Application Data

(63) Continuation of application No. PCT/JP2010/063573, filed on Aug. 10, 2010.

(30) Foreign Application Priority Data

Aug. 11, 2009 (JP) .................................. 2009-186269
Sep. 14, 2009 (JP) .................................. 2009-211826

(51) Int. Cl.
*B01J 38/10* (2006.01)
*C07C 2/02* (2006.01)

(52) U.S. Cl.
USPC ................ 502/53; 502/34; 585/643; 585/644

(58) Field of Classification Search
USPC ............ 585/643, 644, 638, 639, 640; 502/34, 502/53
See application file for complete search history.

(56) References Cited

U.S. PATENT DOCUMENTS 4,021,502 A * 5/1977 Plank et al. .................... 585/533
4,358,395 A * 11/1982 Haag et al. ...................... 502/53
4,417,083 A 11/1983 Bernard et al.
4,440,871 A * 4/1984 Lok et al. ...................... 502/214

(Continued)

FOREIGN PATENT DOCUMENTS

CN 101410353 A 4/2009
JP 52-052888 4/1977

(Continued)

OTHER PUBLICATIONS

IZA Data, International Zeolite Association Structure Commission database available at www.iza-strucure.org, accessed Sep. 20, 2012.*

(Continued)

*Primary Examiner* — In Suk Bullock
*Assistant Examiner* — Bradley Etherton
(74) *Attorney, Agent, or Firm* — Oblon, Spivak, McClelland, Maier & Neustadt, L.L.P.

(57) ABSTRACT

A method for manufacturing a catalyst, which comprises regenerating a catalyst comprising a CHA zeolite as an active ingredient and having an ethylene conversion lowered through reaction of producing propylene by bringing into contact with ethylene in a vapor phase, by bringing the catalyst into contact with a gas which does not comprise oxygen and comprises hydrogen having a hydrogen partial pressure of 0.01 MPa or more as an absolute pressure thereof.

7 Claims, 10 Drawing Sheets

(56) References Cited

U.S. PATENT DOCUMENTS

| | | | | |
|---|---|---|---|---|
| 4,527,001 | A | * | 7/1985 | Kaiser .................. 585/643 |
| 4,717,782 | A | * | 1/1988 | Garwood et al. ........... 585/531 |
| 4,777,156 | A | * | 10/1988 | Forbus et al. ............ 502/53 |
| 4,871,446 | A | | 10/1989 | Herbst et al. |
| 4,925,996 | A | * | 5/1990 | Mazurek ................. 585/312 |
| 4,961,907 | A | | 10/1990 | Herbst et al. |
| 5,200,375 | A | * | 4/1993 | Dessau .................. 502/53 |
| 6,448,197 | B1 | * | 9/2002 | Liu et al. ............... 502/210 |
| 6,632,765 | B1 | * | 10/2003 | Chen .................... 502/53 |
| 6,987,078 | B2 | | 1/2006 | Kelly et al. |
| 2004/0063567 | A1 | * | 4/2004 | Ginosar et al. ........... 502/34 |
| 2007/0129589 | A1 | | 6/2007 | Iwamoto et al. |
| 2010/0222203 | A1 | | 9/2010 | Baba et al. |

FOREIGN PATENT DOCUMENTS

| | | |
|---|---|---|
| JP | 55-088857 | 7/1980 |
| JP | 57-024316 | 2/1982 |
| JP | 63-069534 | 3/1988 |
| JP | 2001-096173 | 4/2001 |
| JP | 2003-026613 | 1/2003 |
| JP | 2007-191444 | 8/2007 |
| JP | 2007-291076 | 11/2007 |
| JP | 2007-537028 | 12/2007 |
| WO | WO 2005/023420 | 3/2005 |

OTHER PUBLICATIONS

International Search Report issued Nov. 16, 2010 in PCT/JP2010/063573 filed Aug. 10, 2010.
Combined Chinese Office Action and Search Report issued Aug. 23, 2013, in Chinese Patent Application No. 201080036013.4 with English translation and English translation of category of cited documents.

* cited by examiner

US 8,647,999 B2

METHOD FOR REGENERATING A CATALYST CONTAINING A CHA ZEOLITE

TECHNICAL FIELD

The present invention relates to a method for manufacturing a catalyst, and more precisely to a method for manufacturing a catalyst which comprises regenerating a catalyst comprising a zeolite as an active ingredient and having an ethylene conversion lowered through a reaction of producing propylene by bringing into contact with ethylene in a vapor phase, by bringing the catalyst into contact with a gas which does not comprise oxygen and comprises hydrogen, and to a method for manufacturing propylene using the catalyst produced according to the method.

BACKGROUND ART

Heretofore, as a method for manufacturing propylene, generally employed is a steam cracking method for naphtha, or a fluid catalytic cracking method for vacuum gas oil. The steam cracking method produces a large quantity of ethylene in addition to propylene, in which it is difficult to significantly change the production ratio of propylene to ethylene and it is therefore difficult to meet the supply-demand balance of propylene and ethylene. Accordingly, a technique is desired for manufacturing propylene at a high yield from ethylene alone as a starting material.

Regarding the technique, Patent Reference 1 discloses a method for manufacturing propylene from ethylene as a starting material, in which an aluminosilicate catalyst having a pore size of less than 0.5 nm is used. According to the method, propylene can be produced efficiently from ethylene.

In hydrocarbon conversion reaction, in general, the catalyst is deactivated by coke deposition thereto. The same shall apply also to the reaction of producing propylene form ethylene, in which, therefore, coke must be removed for catalyst regeneration. In general, the deposited coke is burnt and removed away with a gas comprising oxygen.

In Patent Reference 2, a zeolite-β catalyst deactivated in aromatic alkylation reaction is regenerated by oxidizing the deposited coke with an oxygen-containing gas.

In Patent Reference 3, for regenerating the catalyst used in fixed bed vapor-phase reaction, an oxygen-containing vapor is circulated through the system for coke removal.

PRIOR ART REFERENCES

Patent References

[Patent Reference 1] JP-A 2007-291076
[Patent Reference 2] JP-T 2007-537028
[Patent Reference 3] JP-A 2001-96173

SUMMARY OF THE INVENTION

Problems that the Invention is to Solve

The present inventors's investigation have revealed that, in a method for manufacturing propylene by bringing ethylene into contact with a catalyst having zeolite as an active ingredient, when a fresh catalyst is used, though the ethylene conversion in the primary-stage reaction is extremely high, propylene is produced little but paraffins such as propane are mainly produced.

With the lapse of the reaction time, coke begins to deposit on the catalyst, and the ethylene conversion gradually lowers, but the main product is propylene. Accordingly, irrespective of high ethylene conversion, high propylene selectivity can be expressed and the best reaction result can be obtained in industrial-scale manufacture.

However, it is known that, with further increase in the coke deposition after further lapse of reaction time, the ethylene conversion greatly lowers though the high propylene selectivity could be kept as such. This may be presumed because the reaction with a catalyst with coke deposition thereto can express high propylene selectivity and the coke deposition to the catalyst may have a condition suitable to manufacture of propylene through contact of ethylene with the catalyst.

Accordingly, in industrial-scale manufacture of propylene by bringing ethylene into contact with a catalyst having zeolite as an active ingredient, catalyst generation for coke removal is necessary for reaction at high ethylene conversion.

However, in ordinary catalyst regeneration with an oxygen-containing gas for coke removal from catalyst, the ethylene conversion of the regenerated catalyst could be restored to the level thereof of fresh catalyst, but this involves a problem in that the propylene selectivity of the regenerated catalyst also lowers to the level thereof of fresh catalyst.

This may be presumed because, in the case of regeneration with an oxygen-containing gas, coke would be completely removed. Accordingly, it is desired to establish a catalyst regeneration method capable of still maintaining the high propylene selectivity even after the catalyst regeneration.

To solve the above-mentioned problems, the present inventors investigated a method of partially removing coke by changing the time for catalyst generation with an oxygen-containing gas, and as a result, the ethylene conversion was regenerated partially, but the propylene selectivity was low as compared with that in the case where fresh catalyst was used and coke deposited.

This may be presumed because the property of the coke that has deposited with the lapse of reaction time would differ from that of the coke after catalyst regeneration and the coke necessary for high propylene selectivity would be removed through the catalyst regeneration operation with an oxygen-containing gas.

In this description, "coke" means the generic term including hydrocarbon and carbon existing at least in any of the catalyst surface and inside the catalyst.

An object of the present invention is to provide a method for manufacturing a catalyst having a high ethylene conversion and maintaining a high propylene selectivity, which has solved the above-mentioned prior-art problems, and to provide a method for manufacturing propylene using the catalyst thus produced according to the method.

Means for Solving the Problems

The inventors have assiduously studied for the purpose of solving the above-mentioned problems and, as a result, have found that, in a reaction of synthesizing propylene in a vapor phase from ethylene as a starting material, when the catalyst of which the ethylene conversion has lowered is brought into contact with a gas which does not comprise oxygen and comprises hydrogen having a hydrogen partial pressure of 0.01 MPa or more as an absolute pressure thereof, then the catalyst can be regenerated to the state still maintaining the high propylene selectivity after the regeneration, as compared with the conventional regeneration method of removing coke with an oxygen-containing gas. The invention has been performed based on these views.

Specifically, a gist of the invention resides in the following (1) to (8):

(1) A method for manufacturing a catalyst, which comprises regenerating a catalyst comprising a zeolite as an active ingredient and having an ethylene conversion lowered through a reaction of producing propylene by bringing into contact with ethylene in a vapor phase, by bringing the catalyst into contact with a gas which does not comprise oxygen and comprises hydrogen having a hydrogen partial pressure of 0.01 MPa or more as an absolute pressure thereof.

(2) The method for manufacturing a catalyst according to (1), wherein a temperature at which the catalyst is regenerated is 300° C. or more and 750° C. or less.

(3) The method for manufacturing a catalyst according to (1) or (2), wherein the catalyst is regenerated until the ethylene conversion reaches the range from 50 to 90% and a propylene selectivity reaches 40% or more, when the regenerated catalyst is brought into contact with ethylene in a vapor phase to produce propylene at the same temperature, under the same pressure and at the same space velocity as those in the reaction to produce propylene.

(4) The method for manufacturing a catalyst according to any one of (1) to (3), wherein the catalyst is a metal-supported zeolite.

(5) The method for manufacturing a catalyst according to any one of (1) to (4), wherein the zeolite has a pore size of less than 0.6 nm.

(6) The method for manufacturing a catalyst according to any one of (1) to (5), wherein the zeolite is a zeolite having a CHA structure.

(7) A method for manufacturing propylene, comprising using the catalyst manufactured in the method according to any one of (1) to (6) to produce propylene from ethylene.

(8) The manufacture method according to (7), wherein a device for regenerating a catalyst is attached to a reactor in which propylene is produced from ethylene, the catalyst taken out of the reactor is transferred to the device, and the regenerated catalyst is returned back to the reactor to perform the reaction.

Advantage of the Invention

The catalyst regenerated and produced according to the method of the invention maintains a propylene selectivity at the same level as that of the propylene selectivity having increased through contact with ethylene of the same and fresh catalyst, and has a high ethylene conversion, and therefore the catalyst can maintain a predetermined propylene selectivity in repetition of reaction-regeneration and can provide an industrially excellent propylene manufacture method of attaining a stable propylene yield.

MODE FOR CARRYING OUT THE INVENTION

Figure 1:
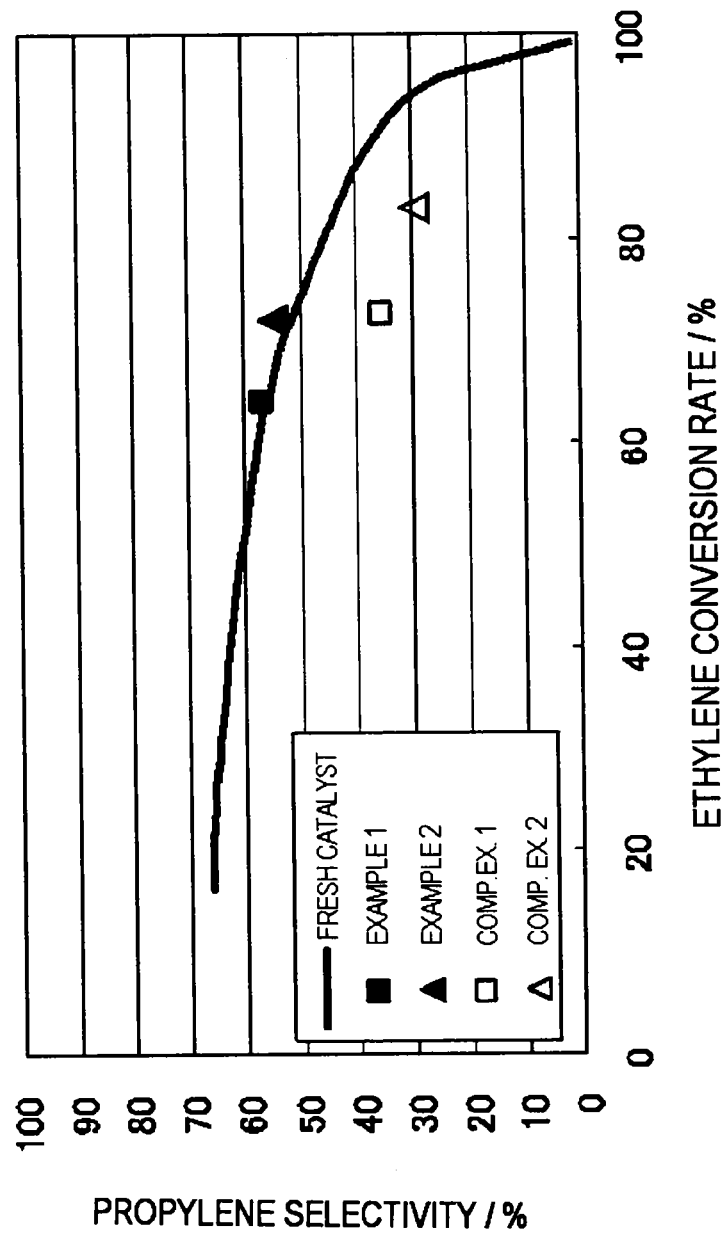
FIG. 1 It is a view showing the relationship between the ethylene conversion and the propylene selectivity of an unregenerated catalyst, the regenerated catalyst of Examples 1 and 2 and the regenerated catalyst of Comparative Examples 1 and 2.

Typical embodiments of carrying out the invention are concretely described below; however, not overstepping the scope and the sprit thereof, the invention should not be limited to the following embodiments.

The zeolite catalyst manufacture method of the invention is characterized in that, in a reaction of producing propylene by bringing ethylene into contact with a catalyst comprising a zeolite as an active ingredient (this may be herein referred to as "zeolite catalyst") in a vapor phase, the catalyst of which the ethylene conversion has lowered owing to coke deposition thereto, is brought into contact with a gas which does not comprise oxygen and comprises hydrogen having a hydrogen partial pressure of 0.01 MPa or more as an absolute pressure thereof to regenerate the catalyst.

The propylene manufacture method of the invention is characterized by using the zeolite catalyst produced according to the above-mentioned method to produce propylene from ethylene.

In the propylene manufacture method of using the catalyst of the invention, when the zeolite catalyst is brought into contact with ethylene in a vapor phase, then it brings about two reactions of carbon-carbon bond forming reaction and carbon-carbon bond cutting reaction to produce propylene.

In this reaction, in case where a fresh zeolite catalyst is used, the ethylene conversion is high but the propylene selectivity is low in the primary stage of the reaction, and with the progress of the reaction (with the activity reduction owing to coke deposition to the catalyst), the propylene selectivity increases and is kept nearly at the highest level.

However, the ethylene conversion gradually lowers owing to coke deposition, and the catalyst is deactivated. In this description, "ethylene conversion" and "propylene selectivity" are the data to be computed according to the methods described in the section of Examples given below. The details are described below.

(1) Catalyst Manufacture Method

The catalyst manufacture method of the invention comprises recovering the ethylene conversion of a catalyst, which comprises a zeolite as an active ingredient (this may be herein referred to as "zeolite catalyst") and catalyzes reaction of producing propylene from ethylene, and has the ethylene conversion lowered through the reaction, according to the method to be mentioned below with maintaining the propylene selectivity thereof as such.

Catalyst regeneration as referred to herein means that the catalyst having the ethylene conversion lowered through the above-mentioned reaction is recovered to have an increased ethylene conversion with maintaining the propylene selectivity thereof.

The catalyst (zeolite catalyst) for use in the invention is meant to indicate a catalyst which comprises a zeolite as an active ingredient and has the ability to produce propylene from ethylene under a suitable temperature condition.

The zeolite as the active ingredient may be used as the catalyst for the reaction directly as it is, or may be granulated/shaped with a substance or binder inert to the reaction, or these may be mixed for use in the reaction.

The substance or binder inert to the reaction includes, for example, alumina, alumina sol, silica, silica gel, quartz and their mixtures.

Zeolite for use herein is a crystalline substance in which $TO_4$ units (T is the center atom) each having a tetrahedral structure are three-dimensionally linked to each other via the O atom therebetween to form opened regular micropores.

Concretely, for example, it includes silicates, phosphates, germanium salts, arsenates and the like described in the Structure Committee Data Collection of the International Zeolite Association (this may be herein referred to as "IZA").

The silicates include, for example, aluminosilicates, gallosilicates, ferrisilicates, titanosilicates, borosilicates and the like.

The phosphates include, for example, aluminophosphates, gallophosphates, beryllophosphates and the like.

The germanium salts include, for example, aluminogermanium salts and the like; and the arsenates include, for example, aluminoarsenates and the like.

The aluminophosphates include, for example, silicoaluminophosphates in which the T atoms are partly substituted with Si, as well as those containing a divalent or trivalent cation such as Ga, Mg, Mn, Fe, Co and Zn.

Not specifically defined, the mean pore size of the zeolite is, in general, preferably less than 0.6 nm, more preferably 0.5 nm or less.

The mean pore size indicates the crystallographic free diameter of the channels defined by IZA.

The mean pore size of less than 0.6 nm means that, when the pores (channels) are true circles, the mean diameter of the true circles is less than 0.6 nm, but when the pores are ovals, the minor diameter thereof is less than 0.6 nm.

As the active ingredient of the invention, zeolite having a mean pore size of less than 0.6 nm is used, with which propylene can be produced at a high yield from ethylene. Though not clear, the effect and the mechanism may be considered because of the presence of strong acid sites to activate ethylene and because of the small pore size to selectively produce propylene.

Specifically, through the fine pores having a mean pore size of less than 0.6 nm, propylene as the reaction product (intended product) could go out, but butene, pentene and others as the by-products are kept remaining inside the pores as their molecules are too large, and after degraded into smaller olefins such as propylene and the like, they may go out through the pores. It may be considered that, owing to this mechanism, the propylene selectivity could be improved.

Also not specifically defined, the lowermost limit of the mean pore size of zeolite is, in general, preferably 0.2 nm or more, more preferably 0.3 nm or more. When the mean pore size is 0.2 nm or more, then the pores can prevent the problem that ethylene and propylene could not pass through them and can prevent the problem that the reaction between ethylene and the active sites is retarded to lower the reaction speed.

The number of oxygen atoms constituting the pore of zeolite is not specifically defined. In general, a structure containing a 8-membered oxygen ring or a 9-membered oxygen ring is preferred, and a structure of a 8-membered oxygen ring alone is more preferred.

The structure containing the 8-membered oxygen ring or 9-membered oxygen ring means that the pore of zeolite is formed of a ring structure of 8 or 9 $TO_4$ units (where T is Si, P, Ge, Al, Ga or the like).

Zeolite composed of a 8-membered oxygen ring structure alone includes, for example, AFX, CAS, CHA, DDR, ERI, ESV, GIS, GOO, ITE, JBW, KFI, LEV, LTA, MER, MON, MTF, PAU, PHI, RHO, RTE, RTH, as indicated by the code defined by IZA.

Zeolite containing a 9-membered oxygen ring structure and having pores alone of not larger than 9-membered oxygen rings include, for example, NAT, RSN, STT, as indicated by the code defined by IZA.

Not specifically defined, the framework density of zeolite is preferably 18.0 or less, more preferably 17.0 or less. In general, it is preferably 13.0 or more, more preferably 14.0 or more.

The framework density (unit: $T/nm^3$) means the number of the T atoms (the atoms constituting the zeolite framework, except oxygen atoms) existing in the unit volume (1 $nm^3$) of zeolite, and the value is determined by the structure of zeolite.

From the viewpoint relating to the above-mentioned structure, the framework structure of zeolite that serves as the active ingredient of the catalyst of the invention is preferably AFX, CHA, ERI, LEV, RHO or RTH, more preferably CHA.

The zeolite having a CHA structure concretely includes, for example, silicates and phosphates.

As described above, the silicates include, for example, aluminosilicates, gallosilicates, ferrisilicates, titanosilicates, borosilicates and the like.

The phosphates include, for example, aluminophosphates comprising aluminium and phosphorus (ALPO-34), silicoaluminophosphates comprising silicon, aluminium and phosphorus (SAPO-34).

Of those, preferred are aluminosilicates and silicoaluminophosphates, and more preferred are aluminosilicates having a high acid strength and attaining a high ethylene conversion.

Zeolite for use for the catalyst of the invention is generally a proton-exchange type, which may be partly exchanged with an alkali metal such as Na and K; an alkaline earth metal such as Mg and Ca; or a transition metal such as Cr, Cu, Ni, Fe, Mo, W, Pt and Re.

Except in the ion-exchange sites, zeolite may be metal-supported with an alkali metal such as Na and K; an alkaline earth metal such as Mg and Ca; or a transition metal such as Cr, Cu, Ni, Fe, Mo, W, Pt and Re. In general, the metal support may be attained according to an equilibrium adsorption method, an evaporation-to-dryness method or an impregnation method such as a pore-filling method.

In case where zeolite is a silicate, the molar ratio of $SiO_2/M_2O_3$ (where M means a trivalent metal such as aluminium, gallium, iron, titanium and boron) is, though specifically defined, generally preferably 5 or more, more preferably 10 or more, and is generally preferably 1000 or less. When the value is 5 or more, then the durability of the catalyst may be prevented from lowering; and when it is 1000 or less, then the ethylene conversion may be prevented from lowering.

In case where zeolite is a phosphate, the molar ratio (Al+P)/Si of the silicoaluminophosphate, or the molar ratio (Al+

P/M of the divalent metal-having metalloaluminosilicate (where M is a divalent metal) is, though not specifically defined, generally preferably 5 or more, more preferably 10 or more, and is generally preferably 500 or less. When the value is 5 or more, then the durability of the catalyst may be prevented from lowering; and when it is 500 or less, then the catalytic activity may be prevented from lowering.

The acid amount in the outer surface of zeolite for use in the catalyst of the invention (this may be herein referred to as "outer surface acid amount") is generally preferably 5% or less relative to the total acid amount in zeolite (this may be herein referred to as "total acid amount"), more preferably 4.5% or less, even more preferably 3.5% or less. The acid amount in the outer surface is preferably as small as possible, and its lowermost limit is not specifically defined.

When the outer surface acid amount relative to the total acid amount is 5% or less, then the side reaction to occur in the outer surface of zeolite to lower the propylene selectivity may be prevented. This may be considered because, although the formation of products having $C_4$ or more is easily occurred when the reaction on the outer surface acid sites is occurred since the reaction on the outer surface would not be given any morphology-selective restriction, the reaction on the outer surface is hardly occurred by setting the outer surface acid amount relative to the total acid amount to 5% or less to prevent the formation of products having $C_4$ or more. In addition, this also may be considered because propylene produced in the pores of the catalyst could be prevented from again reacting with the outer surface acid sites to cause any side reaction.

The outer surface acid amount in zeolite means the overall amount of the acid sites existing in the outer surface of zeolite. The outer surface acid amount is determined concretely as follows. Zeolite is pre-dried in vacuum at 500° C. for 1 hour, and then brought into contact with a pyridine vapor at 150° C. to adsorb it, thereafter the excessive pyridine is removed by actuated evacuation and He flow at 150° C., and the thus-processed zeolite is heated according to a heating desorption method at a heating speed of 10° C./min, in which the pyridine removal per the unit weight of zeolite in a range of from 150 to 800° C. is measured, and this value is the outer surface acid amount in zeolite.

The total acid amount in zeolite is determined as follows. Zeolite is pre-dried in a He flow at 500° C. for 1 hour, then brought into contact with a 5 vol. % ammonia/helium at 100° C. to adsorb it, then further brought into contact with a water vapor at 100° C. to remove the excessive ammonia, and the thus-processed zeolite is heated according to a heating desorption method at a heating speed of 10° C./min, in which the ammonia removal per the unit weight of zeolite in a range of from 100 to 800° C. is measured, and this value is the outer total acid amount in zeolite.

The total acid amount in zeolite for use as the active ingredient of the catalyst of the invention is generally preferably 4.8 mmol/g or less, more preferably 2.8 mmol/g or less. In general, the amount is preferably 0.15 mmol/g or more, more preferably 0.30 mmol/g or more.

When the total acid amount in zeolite is 4.8 mmol/g or less, then the catalyst deactivation owing to coke deposition may be prevented and aluminium may be prevented from leaving away from the framework. In addition, the acid strength per the acid site may be prevented from lowering. When the total acid amount in zeolite is 0.15 mmol/g or more, then the ethylene conversion reduction owing to the insufficient acid amount may be prevented.

The reduction in the ratio of the outer surface amount to the total acid amount may be attained according to a known ordinary method, for example, according to a method of silylating the outer surface of zeolite, a method of steaming zeolite, a method of processing zeolite with a dicarboxylic acid or the like. The treatment may be attained along with the treatment for metal support to be mentioned below, or may be attained before or after the treatment for metal support.

The silylation of the outer surface of zeolite may be attained according to a known silylation method such as a liquid-phase silylation method or a vapor-phase silylation method with a suitably silylating agent. According to the method, the outer surface acid amount in zeolite can be reduced.

The silylating agent includes, for example, quaternary alkoxysilanes such as tetramethoxysilane and tetraethoxysilane; tertiary alkoxysilanes such as trimethoxymethylsilane and triethoxymethylsilane; secondary alkoxysilanes such as dimethoxydimethylsilane and diethoxydimethylsilane; primary alkoxysilanes such as methoxytrimethylsilane and ethoxytrimethylsilane; chlorosilanes such as tetrachlorosilane, dimethyldichlorosilane and trimethylchlorosilane.

Of those, alkoxysilanes are preferred in liquid-phase silylation; and as the alkoxysilanes, preferred is tetraethoxysilane.

Chlorosilanes are preferred in vapor-phase silylation; and as the chlorosilanes, preferred is tetrachlorosilane.

Not specifically defined, the solvent for use in the liquid-phase silylation method includes organic solvents such as benzene, toluene and hexamethyldisiloxane; and water.

In the liquid-phase silylation method, the ratio of silylating agent/zeolite (mol/mol) in the solution to be treated is generally preferably 5 or less, more preferably 3 or less. The ratio is generally preferably 0.005 or more, more preferably 0.1 or more.

When the ratio of silylating agent/zeolite (mol/mol) in the solution to be treated is 5 or less, then the pores could be prevented from being filled up by oversilylation. When the ratio is 0.005 or more, then the silylation may be enough and the outer surface acid amount could be reduced sufficiently.

Depending on the type of the silylating agent and the solvent used, the silylation temperature is generally preferably 140° C. or less, more preferably 120° C. or less. The temperature is generally preferably 20° C. or more, more preferably 40° C. or more.

When the silylation temperature is 140° C. or less, then the silylation efficiency could be prevented from lowering owing to liquid evaporation. When the silylation temperature is 20° C. or more, then the silylation speed could be prevented from lowering.

The silylation time is generally preferably 0.5 hours or more, more preferably 2 hours or more. The uppermost limit of the silylation time is not specifically defined. When the silylation time is 0.5 hours or more, then sufficient silylation could be secured and the outer surface acid amount could be reduced sufficiently.

In the vapor-phase silylation method, the weight of the deposited silica is generally preferably 20% by weight or less relative to zeolite, more preferably 18% by weight or less. The weight of the deposited silica is generally preferably 0.1% by weight or more, more preferably 1% by weight or more.

When the weight of the deposited silica is 20% by weight or less, then the pores could be prevented from being filled up by oversilylation. When the amount is 0.1% by weight or more, then the silylation may be enough and the outer surface acid amount could be reduced sufficiently.

The vapor-phase silylation temperature is generally preferably 20° C. or more, more preferably 100° C. or more. In general, the temperature is preferably 500° C. or less, more preferably 400° C. or less.

When the vapor-phase silylation temperature is 20° C. or more, then the silylation could be prevented from hardly progressing. When the vapor-phase silylation temperature is not higher than 500° C., then the silylating agent could be prevented from decomposing and the zeolite framework could also be prevented from being broken.

The temperature of the steaming treatment to zeolite is preferably at a temperature of 400° C. or more, more preferably 500° C. or more. Also preferably, the temperature is 700° C. or less, more preferably 650° C. or less.

When the temperature of the steaming treatment to zeolite is 400° C. or more, zeolite could sufficiently enjoy the steaming effect; and when the temperature is 700° C. or less, then the zeolite structure could be prevented from being broken.

The steam may be diluted with an inert gas such as helium or nitrogen. In this case, the steam concentration is generally preferably 3% by volume or more, more preferably 5% by volume or more. The uppermost limit of the concentration is not specifically defined, and treatment with 100% steam is possible.

Prior to steaming, zeolite may be physically mixed with a compound comprising an alkaline earth metal. The compound comprising an alkaline earth metal includes, for example, calcium carbonate, calcium hydroxide, and magnesium carbonate. Of those, preferred is calcium carbonate.

The amount of the compound comprising an alkali metal salt is preferably 0.5% by weight or more relative to zeolite, more preferably 3% by weight or more. The amount is also preferably 45% by weight or less, more preferably 40% by weight or less. When zeolite is mixed with such a compound comprising an alkaline earth metal, then the acid amount in zeolite could be prevented from increasing more than necessary.

Steaming may be attained in the condition where an organic matter exists inside the pores for the purpose of selective aluminium removal from the outer surface to reduce the outer surface acid amount.

The organic matter includes, for example, the structure directing agent used in zeolite synthesis, and the coke produced through the reaction. Of those organic matters, the structure directing agent remains inside the pores of the synthesized zeolite. The coke may be made to remain inside the pores according to a method of circulating a hydrocarbon at a temperature of 200° C. or more around the catalyst.

It may be considered that the treatment with a dicarboxylic acid could promote the removal of aluminium and the like from the metal skeleton in the zeolite framework, thereby reducing the acid amount in the treated zeolite. However, the molecular size of a dicarboxylic acid is larger than the pore size of zeolite and therefore the acid could not come in the pores. Accordingly, treatment of zeolite with a dicarboxylic acid selectively reduces the acid amount in the outer surface of zeolite.

The dicarboxylic acid includes, for example, oxalic acid, malonic acid, succinic acid, glutaric acid, adipic acid, maleic acid, phthalic acid, isophthalic acid, fumaric acid, tartaric acid. Their mixture is also usable here. Of those, preferred is oxalic acid.

The dicarboxylic acid is mixed with zeolite as its solution. The concentration of the dicarboxylic acid in its solution is generally preferably 0.01 M or more, more preferably 1 M or more. The concentration is generally preferably 4 M or less, more preferably 3 M or less.

The temperature in mixing the dicarboxylic acid and zeolite is generally preferably 15° C. or more, more preferably 50° C. or more. The temperature is generally preferably 95° C. or less, more preferably 85° C. or less.

Mixing zeolite therewith may be repeated twice or more for promoting the aluminium removal from the zeolite surface.

The treatment of the zeolite with a dicarboxylic acid may be attained in the condition where an organic matter exists inside the pores for the purpose of more selective aluminium removal from the outer surface of zeolite. The organic matter includes, for example, the structure directing agent used in zeolite synthesis, the coke produced through the reaction and the like.

Of those organic matters, the structure directing agent remains inside the pores of the synthesized zeolite. The coke may be made to remain inside the pores according to a method of circulating a hydrocarbon at a temperature of 200° C. or more around the catalyst.

Zeolite mentioned above may be synthesized according to a known ordinary method, for example, according to a hydrothermal synthesis method, or that is, a method of preparing an aqueous gel of a crystal precursor which comprises a silica material, a hetero element source, and an alkali metal or alkaline earth metal element source, followed by heating it.

After the hydrothermal synthesis thereof, if desired, it may be modified through treatment for acid amount reduction, impregnation, supporting or the like as described above, thereby changing the composition thereof.

Having the physical properties and the composition mentioned above, zeolite for use as an active ingredient of the catalyst of the invention may be prepared in any method.

The zeolite for use as an active ingredient of the catalyst of the invention may support a metal element. Not specifically defined, the metal element may be any one having the ability to promote catalyst regeneration in hydrogen.

Concretely, the metal element includes, for example, Cu, Fe, Co, Cr and Pt; and preferably, the catalyst of the invention comprises, as an active ingredient thereof, zeolite which comprises at least one of those metal elements.

Using the catalyst which comprises, as an active ingredient, zeolite which supports such a metal element may promote catalyst regeneration in hydrogen, and therefore can prevent the ethylene conversion reduction in the presence of hydrogen. This may be considered because the metal active to hydrogenation could promote the removal of coke deposited on the catalyst.

Of the metal which zeolite for use in the invention supports, Cu is most preferred. Not specifically defined, the metal content is preferably 0.01% by mass or more relative to zeolite, and more preferably 10% by mass or less. Also preferably, the metal content is 0.05% by mass or more, and more preferably 5% by mass or less.

The method of introducing a metal element into zeolite is not specifically defined. Preferably, a precursor of the metal is used, and the metal is incorporated into zeolite according to an ion-exchange method or an impregnation method. The metal precursor may be added to the system where zeolite is synthesized according to the above-mentioned hydrothermal synthesis method. One or more such metals may be introduced into zeolite either singly or as combined.

The amount of the metal element to be introduced into zeolite (metal content in zeolite) is generally preferably 0.01% by mass or more relative to the mass of zeolite, more preferably 0.05% by mass or more. Also preferably, the amount is 10% by mass or less, more preferably 5% by mass or less.

When the amount of the metal element to be introduced into zeolite is 0.01% by mass or more, the proportion of the cage where the metal element exists in zeolite could be enough and the effect of metal element introduction could be readily exhibited. When the amount of the metal element to be introduced is 10% by mass or less, then the pores are prevented from being filled up with the metal element and may therefore remain to act effectively.

The metal precursor may be any one capable of dissolving in the solvent used for the introduction, and includes, for example, nitrates, acetates, sulfates, chlorides, ammine complex salts, chlorine complex salts and the like. Of those, preferred are nitrates, acetates and ammine complex salts.

The solvent for use in the ion-exchange method or the impregnation method may be any one capable of dissolving the metal precursor and capable of penetrating into the pores of zeolite. For example, it includes water, methanol, ethanol and the like.

The metal introduction according to an ion-exchange method may be attained according to a known method. The cation for zeolite for use in the ion-exchange method is not specifically defined, for which, in general, usable is any of sodium type, ammonium ion-type, proton-type and the like.

The ion-exchange method is a method to be used in metal introduction into a support having a cation exchangeability, in which the cation on the support is exchanged with the metal cation in a solution for metal introduction into the support.

Regarding the metal precursor and the solvent to be used, the solvent may be any one capable of dissolving the metal precursor, as so mentioned above. The concentration of the metal precursor solution is not specifically defined. When the concentration of the precursor solution is lower, then the metal introduction level may lower, but the metal may be more uniformly introduced into the support.

For the intended ion-exchanging, zeolite may be suspended in a metal precursor solution and stirred therein. The stirring temperature may be from room temperature to around the boiling point of the solvent. The stirring time may be such that the ion-exchanging could reach equilibrium sufficiently within the time, and is generally preferably from 1 to 6 hours or so.

For increasing the metal introduction, the ion-exchanging may be repeated plural times. Zeolite may be separated from the suspension thereof stirred for a predetermined period of time, according to ordinary solid-liquid separation, for example, through filtration or centrifugation.

The atmosphere in which the ion-exchanged support is dried is not specifically defined. For example, the support may be dried in air or in an inert gas or in vacuum. The drying temperature may be from room temperature to around the boiling point of the solvent.

The atmosphere in which the dried support is calcined must be suitably selected depending on the intended state of the metal introduced into the support. For example, when the support is calcined in air, the metal may be introduced into the support as the metal oxide; and when it is calcined in hydrogen, the metal may be introduced thereinto in the form of metal. When the support is calcined in an inert gas, the calcined state thereof may vary depending on the type of the metal precursor used.

The calcination temperature for the dried support may be higher than the decomposition temperature of the metal precursor used, and is generally preferably from 200° C. to 600° C., more preferably from 300° C. to 500° C. When the calcination temperature is the lowermost limit thereof or more, then the metal precursor component may be prevented from remaining therein. When the calcination temperature is the uppermost limit thereof or less, the metal sintering may be prevented and the solid phase reaction between the metal and the support may also be prevented.

The metal introduction according to the impregnation method may be attained in a known method, for example, according to a pore-filling method, an evaporation-to-dryness method, an equilibrium adsorption method or an incipient wetness method.

The pore-filling method is a method used for introducing a metal into pores of a porous support such as zeolite. The pore-filling method comprises adding a metal precursor solution little by little to a support, in an amount corresponding to the pore volume of the carrier, followed by drying and heat-treating for metal introduction thereinto.

The pore volume of the support may be determined according to a known method, for example, by making the support adsorb nitrogen at the liquid nitrogen temperature followed by measuring the nitrogen adsorption.

Regarding the metal precursor and the solvent to be used, the solvent may be any one capable of dissolving the metal precursor and capable of penetrating into the pores of zeolite, as so mentioned above. Not specifically defined, the concentration of the metal precursor solution may be determined in any desired manner depending on the amount of the metal to be introduced.

The impregnation may be attained by repeating an operation of dropwise applying a few drops of a metal precursor solution to a zeolite powder followed by mixing them. In this case, when the speed of dropwise adding the precursor solution is slower and when the mixing is attained more sufficiently, the metal could be more uniformly introduced into the carrier.

The atmosphere in which the metal-immersed zeolite is dried is not specifically defined. For example, it may be dried in air, in an inert gas or in vacuum.

The drying temperature is generally preferably from room temperature to around the boiling point of the solvent. When the drying temperature is lower, then the metal precursor solution more hardly moves and can be therefore more uniformly introduced into the support, but the solvent may remain partly and the drying takes a lot of time. Accordingly, it is desirable that after the support fully dried at a low temperature and then dried at a high temperature for a short period of time, or the support is dried under reduced pressure at a low temperature.

Preferably, the atmosphere in which the dried zeolite is calcined is suitably selected depending on the intended state of the introduction. For example, when calcined in air, the metal may be introduced as the metal oxide; and when calcined in hydrogen, the metal may be introduced thereinto in the form of metal. When calcined in an inert gas, the calcined state may vary depending on the type of the metal precursor used.

The calcination temperature may be higher than the decomposition temperature of the metal precursor used, and is generally preferably from 200° C. to 600° C., more preferably from 300° C. to 500° C. When the calcination temperature is the lowermost limit thereof or more, then the metal precursor component may be prevented from remaining therein. When the calcination temperature is the uppermost limit thereof or less, the metal sintering may be prevented and the solid phase reaction between the metal and zeolite may also be prevented.

The regeneration method for the catalyst having the ethylene conversion lowered, according to the catalyst manufacture method of the invention, is as follows.

The catalyst having the ethylene conversion lowered means the catalyst with which the ethylene conversion has lowered to such a degree that the catalyst enables, as a result of increasing the ethylene conversion thereof, industrial-scale efficient propylene manufacture in the reaction of producing propylene from ethylene by the use of the catalyst.

Concretely, the ethylene conversion of the catalyst having the ethylene conversion lowered is preferably 60% or less as compared with the ethylene conversion in the primary reaction of using the same and fresh catalyst, more preferably 55% or less.

The regeneration method comprises bringing the catalyst into contact with a gas which does not comprise oxygen and comprises hydrogen having a hydrogen partial pressure of 0.01 MPa or more as an absolute pressure thereof. Through regeneration according to the method, the ethylene conversion is recovered to the same level as that in the primary reaction with maintaining the propylene selectivity of the catalyst at the same level as that before the regeneration step.

Not specifically defined, the device for regeneration may be any one in which the catalyst can be brought into contact with a hydrogen-containing gas under the condition mentioned below. For the device, preferably employed is a method of introducing a hydrogen-containing gas into a reactor for reaction of producing propylene from ethylene, without taking out the catalyst from the reactor. As the case may be, the catalyst may be once taken out of the reactor, and is transferred into a separate regenerator that differs from the reactor, and it may be brought into contact with the regenerating gas in the regenerator.

In case where the reactor includes a moving bed or a fluidized, it is desirable that a device for regenerating a catalyst is attached to the reactor, and the catalyst taken out of the reactor is continuously transferred into the device and the catalyst regenerated in the device is continuously returned back to the reactor to attain continuous reaction therein. The catalyst in the system may be replenished, or may be partly purged away during reaction and regeneration.

The hydrogen-containing gas for use for regeneration has a hydrogen partial pressure of 0.01 MPa or more as an absolute pressure thereof, preferably 0.02 MPa or more, more preferably 0.05 MPa or more. When the partial hydrogen pressure is 0.01 MPa or more, then the coke removing speed can be prevented from lowering.

The uppermost limit of the hydrogen partial pressure is not specifically defined, but as the absolute pressure thereof, it is preferably 4 MPa or less, more preferably 1 MPa or less, even more preferably 0.7 MPa or less. The hydrogen partial pressure is preferably higher; however, when it is 4 MPa or less, then it would not require any large energy for production of high-pressure hydrogen and would not require installation of a high-pressure apparatus for the production.

The gas does not comprise oxygen. "The gas does not comprise oxygen" as referred to herein means that the oxygen concentration in the gas is less than 0.1%. When a gas comprising oxygen equal to or more than the range is used, then the propylene selectivity of the catalyst is lower.

From the viewpoint of the safety regarding hydrogen explosion, when the oxygen concentration is more than 5%, then it reaches the explosion limit. Accordingly, the oxygen amount is preferably smaller. When the oxygen concentration is smaller, then the oxygen partial pressure is smaller, and it is desirable since coke removal by hydrogen occurs dominantly.

The lowermost limit is 0% that means the absence of oxygen. In general, the oxygen partial pressure is preferably 0.005 MPa or less, more preferably 0.001 MPa or less, further preferably 0.0001 MPa or less, most preferably 0 MPa.

The method for manufacturing the hydrogen gas to be contained in the hydrogen-containing gas for use in the invention is not specifically defined. For example, any hydrogen gas produced by various methods may be used here in any desired manner, including, for example, one produced through steam reforming of methane and methanol, one produced through partial oxidation of hydrocarbon, one produced through hydrocarbon reforming with carbon dioxide, one produced through gasification of coal, one produced through thermal decomposition of water typically according to an IS (iodine-sulfur) process, one produced through photoelectrochemical reaction, and one produced through electrolysis of water.

Hydrogen mixed with any element other than oxygen or compound may be used as such, or purified hydrogen may be used.

The gas after use for regeneration comprises hydrocarbon in addition to hydrogen, and this may be recycled for regeneration directly as it is or after a part of hydrocarbon is removed from it.

The gas other than hydrogen to be in the hydrogen-containing gas includes, for example, helium, argon, nitrogen, carbon monoxide, carbon dioxide, steam, paraffins such as methane. Of those preferred are helium, argon, nitrogen, carbon dioxide, steam and paraffins as their reactivity with the catalyst is low.

In the regeneration method, the space velocity of the hydrogen-containing gas is not specifically defined, falling within the range within which the catalyst regeneration is possible. Concretely, the speed is preferably from 0.01 $hr^{-1}$ to 500 $hr^{-1}$, more preferably from 0.1 $hr^{-1}$ to 200 $hr^{-1}$, even more preferably from 10 $hr^{-1}$ to 100 $hr^{-1}$.

When the space velocity is defined to be the above-mentioned lowermost limit or more, the hydrogen concentration in the zone from the inlet of the catalyst bed to be regenerated to the outlet thereof may be prevented from lowering, and the concentration of the hydrocarbon removed from the catalyst may be prevented from increasing and the coke removing speed may be prevented from lowering. In addition, the hydrogen concentration difference between the inlet of the catalyst bed and the outlet thereof may be prevented from increasing, therefore facilitating uniform regeneration.

When the space velocity is defined to be the above-mentioned uppermost limit or less, then the necessary amount of the gas for regeneration may be controlled, which is therefore advantageous in point of the cost.

The space velocity is the flow rate of hydrogen per the weight of the catalyst (active ingredient of catalyst). The weight of the catalyst means the weight of the active ingredient (zeolite) which does not comprise the inert ingredient and the binder used for granulation and shaping of the catalyst.

The concentration of hydrogen in the total supply composition to be fed to the regeneration device is preferably higher, and is generally preferably 20% by volume or more, more preferably 60% by volume or more, even more preferably 70% by volume or more. When the hydrogen concentration is 20% by volume or more, then the hydrogen partial pressure may be prevented from lowering and the coke removing speed may be therefore prevented from lowering.

The temperature in the regeneration device (this may be herein referred to as "regeneration temperature") is generally preferably 300° C. or more, more preferably 400° C. or more, even more preferably 450° C. or more. In general, the temperature is preferably 750° C. or less, more preferably 650° C. or less, even more preferably 550° C. or less.

When the regeneration temperature is 400° C. or more, then the system may secure a sufficient regeneration speed and may not take too much time. On the other hand, when the regeneration temperature is 750° C. or less, then the zeolite framework may be prevented from being broken.

The regeneration temperature may be controlled according to a method of controlling the temperature inside the regeneration device or according to a method of controlling the supply gas temperature.

The regeneration time is not specifically defined since its preferred range may vary depending on the condition such as the regeneration temperature. In general, the time is preferably 30 seconds or more, more preferably 1 minute or more. Also preferably, the time is generally 180 minutes or less, more preferably 120 minutes or less.

When the regeneration time is 30 seconds or more, then the coke removal may be prevented from being sufficient and the ethylene conversion in reaction may be prevented from lowering. When the time is 180 minutes or less, then the coke removal may not go on too much and the propylene selectivity may be prevented from lowering.

In case where a fluidized bed regenerator is used, the above-mentioned regeneration time indicates the catalyst retention time in the regenerator.

Preferably, the propylene selectivity of the thus-regenerated catalyst is 70% or more of the uppermost limit of the propylene selectivity of the catalyst; and preferably, the ethylene conversion thereof is from 2 to 4 times before regeneration.

Concretely, when the catalyst used is an Si/Al catalyst, the ethylene conversion of the regenerated catalyst is generally preferably from 50 to 90%, more preferably from 60 to 90%. Also preferably, the propylene selectivity of the regenerated catalyst is generally 40% or more, more preferably 50% or more, and is generally preferably 95% or less.

The ethylene conversion and the propylene selectivity are meant to indicate the ethylene conversion and the propylene selectivity, respectively, in production of propylene by bringing ethylene into contact with the regenerated catalyst in a vapor phase, at the same temperature, pressure and space velocity as those in the propylene manufacture method to be mentioned below.

The temperature is preferably 200° C. or more, more preferably 300° C. or more. In general, the temperature is preferably 700° C. or less, more preferably 600° C. or less.

The pressure is preferably 2 MPa or less, more preferably 1 MPa or less, even more preferably 0.7 MPa or less. Also preferably, the pressure is 1 kPa or more, more preferably 50 kPa or more.

The space velocity is preferably from 0.01 $hr^{-1}$ to 500 $hr^{-1}$, more preferably from 0.1 $hr^{-1}$ to 100 $hr^{-1}$.

That is, according to the invention, the ethylene conversion of the catalyst can be recovered to such a degree that the propylene selectivity thereof is not lowered to the low level as in the primary reaction.

The catalyst regeneration may be suitably performed within the range of attaining the object of the invention, and the time for initiating the regeneration may be suitably selected depending on the catalyst and the reaction condition, and is therefore not specifically defined. Preferably, when the ethylene conversion has become 60% or less, more preferably 55% or less, as compared with that with the same and fresh catalyst in the primary reaction, then the regeneration may be started.

The discharge gas from the catalyst regeneration device comprises hydrocarbon formed through hydrogenolysis of the coke deposition to the catalyst, in addition to hydrogen therein. The hydrocarbon to be in the gas includes, for example, ethylene, propylene, ethane, propane and the like.

The discharge gas from the regenerator may be used as fuel as such, but preferably, the hydrocarbon is recovered. For recovering it, for example, employable is a method introducing the regenerator discharge gas into the reactor inlet along with the starting ethylene thereinto; a method of mixing the regenerator discharge gas and the reactor discharge gas and separating them; a method of separately separating and purifying the regenerator discharge gas and the reactor discharge gas.

For separating hydrogen and hydrocarbon from each other, employable is any known method. For example, employable is distillation, membrane separation, PSA, absorption separation or the like.

(2) Method for Manufacturing Propylene:

The propylene manufacture method of the invention is characterized by using the catalyst produced according to the above-mentioned method and producing propylene from ethylene.

In the propylene manufacture method of the invention, propylene may be produced according to a known ordinary method, or that is, according to a method of bringing a starting material ethylene into contact with the above-mentioned regenerate catalyst under a suitable reaction condition in a suitable reactor.

The starting material ethylene is not specifically defined. For example, any ethylene produced by various methods may be used here in any desired manner, including, for example, one produced from a petroleum supply source according to a catalytic cracking method or a steam cracking method, one produced from a hydrogen/CO mixed gas obtained in gasification of coal, through Fischer-Tropsch synthesis, one produced through dehydration or oxidative dehydration of ethane, one produced through metathesis reaction or homologation reaction of propylene, one produced through MTO (methanol to olefin) reaction, one produced through dehydration of ethanol, one produced through oxidative coupling reaction of methane, and the like.

It may comprise any element and compound other than ethylene to be derived from various production methods, and may be used here directly as it is, or purified ethylene may be used here. From the viewpoint of the economical aspect, preferred is use of unpurified ethylene.

The olefins in the reactor discharge gas may be recycled. The olefin to be recycled is generally unreacted ethylene, but any other olefins may be recycled simultaneously with no problem.

The other olefins are preferably lower olefins. Branched chain olefins hardly penetrate into the pores of zeolite as the size of the molecules thereof is large, and therefore, linear chain butene is more preferred.

At the acid sites existing inside zeolite, ethanol is readily dehydrated and converted into ethylene. Accordingly, ethanol may be directly introduced into the reactor as the starting material.

The type of the reactor is not specifically defined. In general, a continuous-type fixed bed reactor, a moving bed reactor and a fluidized bed reactor may be used. Of those, preferred is a fluidized bed reactor.

In filling the catalyst into the fluidized bed reactor, a granular substance inert to the reaction, such as quartz sand, alumina, silica or silica-alumina may be mixed with the catalyst and filled therein, for the purpose of reducing the temperature distribution of the catalyst bed. In this case, the amount of the granular substance inert to the reaction such as quartz sand is not specifically defined.

The grain size of the granular substance is preferably at the same level as that of the catalyst from the viewpoint of uniformly mixing them.

In case where the catalyst is taken out from the reactor and regenerated as in the above, preferably, a device for catalyst regeneration (this may be herein referred to as "regenerator") is attached to the reactor, and the catalyst taken out of the reactor is transferred to the regenerator and the catalyst regenerated in the regenerator is returned back to attain reaction therein.

In this case, the catalyst may be regenerated to have the above-mentioned, desired ethylene conversion by controlling the retention time of the catalyst in the reactor and in the regenerator.

Before the catalyst taken out of the reactor is transferred to the regenerator, the lower hydrocarbon such as propylene existing inside the catalyst may be recovered. Accordingly, the hydrocarbon loss may be reduced, and in addition, the amount of the hydrocarbon to form in catalyst regeneration may be reduced, therefore resulting in that the amount of hydrogen to be used for regeneration can be reduced.

In case where a fixed bed reactor system is used, preferably, at least two reactors are installed and these are so driven that reaction and catalyst regeneration are alternately effected therein.

The reactor may comprise, in addition to ethylene therein, any vapor inert to the reaction, for example, helium, argon, nitrogen, carbon monoxide, carbon dioxide, hydrogen, water, paraffins, hydrocarbons such as methane, aromatic compounds, and their mixtures.

Of those, preferred are hydrogen and paraffins. When hydrogen exists therein, then coke removal may be attained along with coke deposition occurring therein, and the catalyst activity may be prevented from lowering.

The gas discharged out from the regenerator may be fed to the reactor whereby the hydrocarbon contained in the regenerator discharge gas may be effectively utilized and, in addition, its another advantage is that the reaction may be attained in the presence of hydrogen.

The ethylene concentration in the total supply composition to be fed to the reactor, that is the substrate concentration therein, is not specifically defined. The ethylene concentration in the total supply composition is generally preferably 90 mol % or less, more preferably 70 mol % or less, and is preferably 5 mol % or more.

When the substrate concentration is 90 mol % or less, then remarkable production of aromatic compounds and paraffins may be prevented and the propylene yield may be prevented from lowering. When the substrate concentration is 5 mol % or more, then the reaction speed may be prevented from lowering, and in that condition, a large amount of the catalyst is not needed and the reactor may not be too large. Accordingly, it is desirable that ethylene is optionally diluted with diluent so that the substrate concentration therein could fall within the above range.

Not specifically defined, the space velocity is preferably from $0.01\ hr^{-1}$ to $500\ hr^{-1}$, more preferably from $0.1\ hr^{-1}$ to $100\ hr^{-1}$.

When the space velocity is defined to be the above-mentioned uppermost limit or less, then the ethylene amount in the reactor discharge gas may not be too much and the propylene yield may be prevented from lowering. When the space velocity is defined to be the above-mentioned lowermost limit or more, formation of any adverse by-products such as paraffins may be prevented and the propylene yield may be thereby prevented from lowering.

The space velocity is the flow rate (weight/hr) of ethylene as the starting material per the weight of the catalyst (active ingredient of catalyst). The weight of the catalyst means the weight of the active ingredient (zeolite) which does not comprise the inert ingredient and the binder used for granulation and shaping of the catalyst.

Not specifically defined, the reaction temperature may be any one at which propylene may be produced by bringing ethylene into contact with catalyst. In general, the reaction temperature is preferably 200° C. or more, more preferably 300° C. or more. Also in general, the reaction temperature is preferably 700° C. or less, more preferably 600° C. or less.

When the reaction temperature is 200° C. or more, then the reaction speed may be sufficient and the unreacted starting material may be prevented from remaining much in the system, and the propylene yield may be prevented from lowering. On the other hand, when the reaction temperature is 700° C. or less, then the propylene yield may be prevented from greatly lowering.

The reaction pressure is generally preferably 2 MPa or less as an absolute pressure thereof, more preferably 1 MPa or less, even more preferably 0.7 MPa or less. Also preferably, the pressure is generally 1 kPa or more, more preferably 50 kPa or more.

When the reaction pressure is 2 MPa or less, then the amount of adverse by-products such as paraffins may be reduced and the propylene yield may be prevented from lowering. When the reaction pressure is 1 kPa or more, then the reaction speed may be prevented from lowering.

The reactor discharge gas (reactor discharge fluid) obtained is a mixed gas comprising propylene as the reaction product, the unreacted ethylene, and by-products and diluents. Preferably, the propylene concentration in the mixed gas is generally 1% by weight or more, more preferably 2% by weight or more. Also preferably, the propylene concentration is generally 95% by weight or less, more preferably 80% by weight or less.

At least a part of ethylene in the discharge gas is preferably recycled in the reactor as the starting material therein, as so mentioned in the above.

The by-products include olefins having 4 or more carbon atoms and paraffins.

The discharge gas may be introduced into a known separation/purification apparatus, in which the individual ingredients may be separately recovered, purified, recycled and discharged, and accordingly, propylene as the intended product can be obtained.

EXAMPLES

The invention is described more concretely with reference to the following Examples; however, the invention is not restricted by the following Examples.

In the following Examples and Comparative Examples, the hydrocarbon conversion and selectivity are derived from the found data through computation according to the formulae mentioned below. In the following formulae, " . . . derived carbon molar flow rate (mol/hr)" means the molar flow rate of the carbon atoms constituting the hydrocarbon.

Ethylene Conversion (%)=[[reactor inlet ethylene flow rate (mol/hr)−reactor discharge ethylene flow rate (mol/hr)]/reactor inlet ethylene flow rate (mol/hr)]×100.

Propylene Selectivity (%)=[reactor discharge propylene-derived carbon molar flow rate (mol/hr)/[reactor discharge total carbon molar flow rate (mol/hr)−reactor discharge ethylene-derived carbon molar flow rate (mol/hr)]]×100.

Ethane Selectivity (%)=[reactor discharge ethane-derived carbon molar flow rate (mol/hr)/[reactor discharge total carbon molar flow rate (mol/hr)−reactor discharge ethylene-derived carbon molar flow rate (mol/hr)]]×100.

Propane Selectivity (%)=[reactor discharge propane-derived carbon molar flow rate (mol/hr)/[reactor discharge total carbon molar flow rate (mol/hr)−reactor discharge ethylene-derived carbon molar flow rate (mol/hr)]]×100.

C4 Selectivity (%)=[reactor discharge C4 product-derived carbon molar flow rate (mol/hr)/[reactor discharge total carbon molar flow rate (mol/hr)−reactor discharge ethylene-derived carbon molar flow rate (mol/hr)]]×100.

C5+Selectivity (%)=[reactor discharge C5 product-derived carbon molar flow rate (mol/hr)/[reactor discharge total carbon molar flow rate (mol/hr)−reactor discharge ethylene-derived carbon molar flow rate (mol/hr)]]×100.

Catalyst Preparation Example 1

30 g of a 25% by weight aqueous solution of N,N,N-trimethyl-1-adamantammonium hydroxide, 73 g of an aqueous solution of 1 M sodium hydroxide and 185 g of water were mixed, to which was added 4.5 g of aluminium hydroxide (containing from 50 to 57% in terms of aluminium oxide), and stirred; and as a silica source, 21 g of fumed silica was added thereto and fully stirred.

Further, as a seed crystal, CHA-type zeolite was added to it in an amount of 2% by weight relative to the weight of the fumed silica, and stirred. The resulting gel was fed into an autoclave and heated therein with stirring at 160° C. for 24 hours. The product was filtered, washed with water and dried at 100° C.

After thus dried, this was calcined in an air atmosphere at 580° C. Subsequently, this was ion-exchanged twice with an aqueous solution of 1 M ammonium nitrate at 80° C. for 1 hour. After dried at 100° C., this was calcined in an air atmosphere at 500° C. to give a proton-type CHA-type zeolite. The zeolite is Catalyst A.

The Catalyst A obtained in the above was a proton-type aluminosilicate having a CHA structure; and as confirmed through elementary analysis, the ratio $SiO_2/Al_2O_3$ therein was 16 (by mol), and the pore size was 0.38 nm.

Catalyst Preparation Example 2

The Catalyst A obtained in Preparation Example 1 was silylated with tetraethoxysilane. 10 ml of hexamethyldisiloxane as a solvent, and 5 ml of tetraethoxysilane as a silylating agent were added to 1 g of the Catalyst A, and these were refluxed under stirring at 100° C. for 6 hours. After the treatment, this was filtered for solid-liquid separation, and the resulting zeolite was dried at 100° C. for 2 hours. The zeolite is Catalyst B.

Catalyst Preparation Example 3

The Catalyst A obtained in Preparation Example 1 was processed for making it support copper according to a pore-filling method. The amount of copper that the catalyst supports was 1% by weight relative to zeolite. As the starting material for copper, used was copper(II) nitrate trihydrate, and distilled water was added thereto to make the total amount 0.982 ml, thereby preparing an aqueous copper nitrate solution. A few drops of the aqueous copper nitrate solution were given to 1 g of zeolite, and mixed; and this operation was repeated to thereby make the total amount thereof infiltrated into zeolite. After thus infiltrated, this was dried at room temperature, and then dried at 100° C. for 1 hour. After thus dried, this was calcined in a nitrogen atmosphere at 450° C. to give a copper-supported zeolite.

The copper-supported zeolite prepared in the above was silylated with tetraethoxysilane. 10 ml of hexamethyldisiloxane as a solvent and 2.5 ml of tetraethoxysilane as a silylating agent were added to 1 g of the zeolite, and these were refluxed under stirring at 100° C. for 6 hours. After the treatment, this was filtered for solid-liquid separation, and the resulting silylated zeolite was dried at 100° C. for 2 hours. The zeolite is Catalyst C.

Catalyst Preparation Example 4

59 g of a 25% by weight aqueous solution of N,N,N-trimethyl-1-adamantammonium hydroxide, 146 g of an aqueous solution of 1 M sodium hydroxide and 371 g of water were mixed, to which was added 4.5 g of aluminium hydroxide (containing from 50 to 57% in terms of aluminium oxide), and stirred; and as a silica source, 42 g of fumed silica was added thereto and fully stirred.

Further, as a seed crystal, CHA-type zeolite was added to it in an amount of 2% by weight relative to the weight of the fumed silica, and stirred. The resulting gel was fed into an autoclave and heated therein with stirring at 160° C. for 48 hours. The product was processed in the same manner as in Preparation Example 1 to give a proton-type CHA-type zeolite.

Subsequently, this was silylated in the same manner as in Preparation Example 2. Thus obtained, the zeolite is Catalyst D.

The Catalyst D obtained in the above was a proton-type aluminosilicate having a CHA structure; and as confirmed through elementary analysis, the ratio $SiO_2/Al_2O_3$ therein is 27 (by mol), and the pore size was 0.38 nm.

Example 1

(1) Reaction

Using Catalyst A, propylene was produced from ethylene as a starting material in the manner mentioned below.

For the reaction, used was a fixed-bed flow reactor, in which the quartz reactor tube having an inner diameter of 6 mm was filled with 400 mg of the above zeolite (Catalyst A).

Ethylene and nitrogen were fed into the reactor at an ethylene space velocity of 13 mmol/g-cat·h and in a ratio of ethylene of 30% by volume and nitrogen of 70% by volume, and reacted at 400° C. and 0.1 MPa. In 5 hours and 50 minutes after the start of the reaction, the reaction was terminated. When the fresh catalyst was used, the ethylene conversion at the end of the reaction was from 19 to 20% or so.

Using the catalyst after the reaction (this is herein referred to as "degraded Catalyst A"), the catalyst was regenerated and propylene was produced. The relationship between the ethylene conversion and the propylene selectivity in use of the fresh catalyst is shown by the solid line in FIG. 1.

(2) Catalyst Regeneration and Propylene Production 100 vol. % hydrogen gas was fed to the degraded Catalyst A (ethylene conversion: 19%) at a hydrogen space velocity of 104 mmol/g-cat·h; and at 475° C. and under an absolute pressure of 0.10 MPa (hydrogen partial pressure of 0.10 MPa), the catalyst was regenerated for 60 minutes. The oxygen content of the regeneration gas was 0% by volume (oxygen partial pressure of 0.00 MPa).

After the regeneration, the reaction was again performed under the same condition as above, and at the time of 20 minutes after the start of the reaction, the reaction result was confirmed. Table 1 shows the reaction result; and FIG. 1 shows the relationship between the ethylene conversion and the propylene selectivity.

As in Table 1, the ethylene conversion before regeneration was 19%; but after regeneration with hydrogen, the ethylene conversion was 64% and the propylene selectivity was 57%. From the result, it was found that the propylene selectivity of the hydrogen-regenerated catalyst is nearly at the same level as that of the propylene selectivity of the catalyst before regeneration, and the catalyst is regenerated while maintaining the catalytic capability at the level before regeneration.

Example 2

Under the same condition as in Example 1, an experiment of reaction and regeneration was carried out, in which, however, the degraded catalyst A having an ethylene conversion of 20% was used and the regeneration temperature was 500° C. and the regeneration time was 30 minutes. The reaction result is shown in Table 1; and the relationship between the ethylene conversion and the propylene selectivity is shown in FIG. 1.

As in Table 1, the ethylene conversion before regeneration was 20%; but after regeneration, the ethylene conversion was 72% and the propylene selectivity was 55%. From the result, it was found that the propylene selectivity of the hydrogen-regenerated catalyst is nearly at the same level as that of the propylene selectivity of the catalyst before regeneration, and the catalyst is regenerated while maintaining the catalytic capability at the level before regeneration.

Comparative Example 1

Under the same condition as in Example 1, an experiment was carried out, in which, however, the degraded catalyst A was regenerated as follows. Air (having an oxygen concentration of 20.9% by volume and a hydrogen concentration of 0.5 ppm by volume) was supplied to the degraded catalyst A (ethylene conversion: 20%) in the reaction tube at a space velocity of 199 mmol/g-cat·h, by which the catalyst was regenerated at 500° C. and 0.10 MPa (oxygen partial pressure of 0.021 MPa and hydrogen partial pressure of $5.0 \times 10^{-8}$ MPa) for 5 minutes.

After the regeneration, the reaction was again performed under the same condition as above, and at the time of 20 minutes after the start of the reaction, the reaction result was confirmed. Table 1 shows the reaction result; and FIG. 1 shows the relationship between the ethylene conversion and the propylene selectivity.

As in Table 1, the ethylene conversion before regeneration was 20%; but after regeneration, the ethylene conversion was 73% and the propylene selectivity was 35%. From the result, it was found that the propylene selectivity of the catalyst regenerated with air greatly lowers as compared with the propylene selectivity before regeneration.

Comparative Example 2

Under the same condition as in Comparative Example 1, an experiment of reaction and regeneration was carried out, in which, however, the regeneration time was 6 minutes and 20 seconds. Table 1 shows the reaction result; and FIG. 1 shows the relationship between the ethylene conversion and the propylene selectivity.

As in Table 1, the ethylene conversion before regeneration was 20%; but after regeneration, the ethylene conversion was 83% and the propylene selectivity was 29%. From the result, it was found that the propylene selectivity of the catalyst regenerated with air greatly lowers as compared with the propylene selectivity before regeneration.

TABLE 1

|  | Example 1 | Example 2 | Example 9 | Example 10 | Comparative Example 1 | Comparative Example 2 |
|---|---|---|---|---|---|---|
| Catalyst | A | A | D | D | A | A |
| Regeneration Gas | hydrogen | hydrogen | hydrogen | hydrogen | air | air |
| Regeneration Gas Pressure (MPa) | 0.1 | 0.1 | 0.1 | 0.1 | 0.1 | 0.1 |
| Hydrogen Partial Pressure (MPa) | 0.1 | 0.1 | 0.1 | 0.02 | $5.0 \times 10^{-8}$ | $5.0 \times 10^{-8}$ |
| Oxygen Partial Pressure (MPa) | 0 | 0 | 0 | 0 | 0.021 | 0.021 |
| Ethylene Conversion before regeneration (%) | 19 | 20 | 26 | 36 | 16 | 16 |
| Regeneration Temperature (° C.) | 475 | 500 | 500 | 500 | 500 | 500 |
| Regeneration Time (min) | 60 | 30 | 5 | 5 | 5 | 6.3 |
| Ethylene Conversion (%) | 64 | 72 | 80 | 67 | 73 | 83 |
| Propylene Selectivity (%) | 57 | 55 | 80 | 82 | 35 | 29 |
| Ethane Selectivity (%) | 4 | 6 | 5 | 4 | 4 | 5 |
| Propane Selectivity (%) | 4 | 4 | 7 | 6 | 15 | 22 |
| C4 Selectivity (%) | 18 | 19 | 5 | 5 | 23 | 22 |

TABLE 1-continued

| | Example 1 | Example 2 | Example 9 | Example 10 | Comparative Example 1 | Comparative Example 2 |
|---|---|---|---|---|---|---|
| C5+ Selectivity (%) | 16 | 16 | 2 | 2 | 22 | 21 |
| Difference in Propylene Selectivity* | 1 | 3 | 5 | 3 | −16 | −14 |

*Difference in propylene selectivity between fresh catalyst and regenerated catalyst at the same conversion.

Example 3

Figure 2:
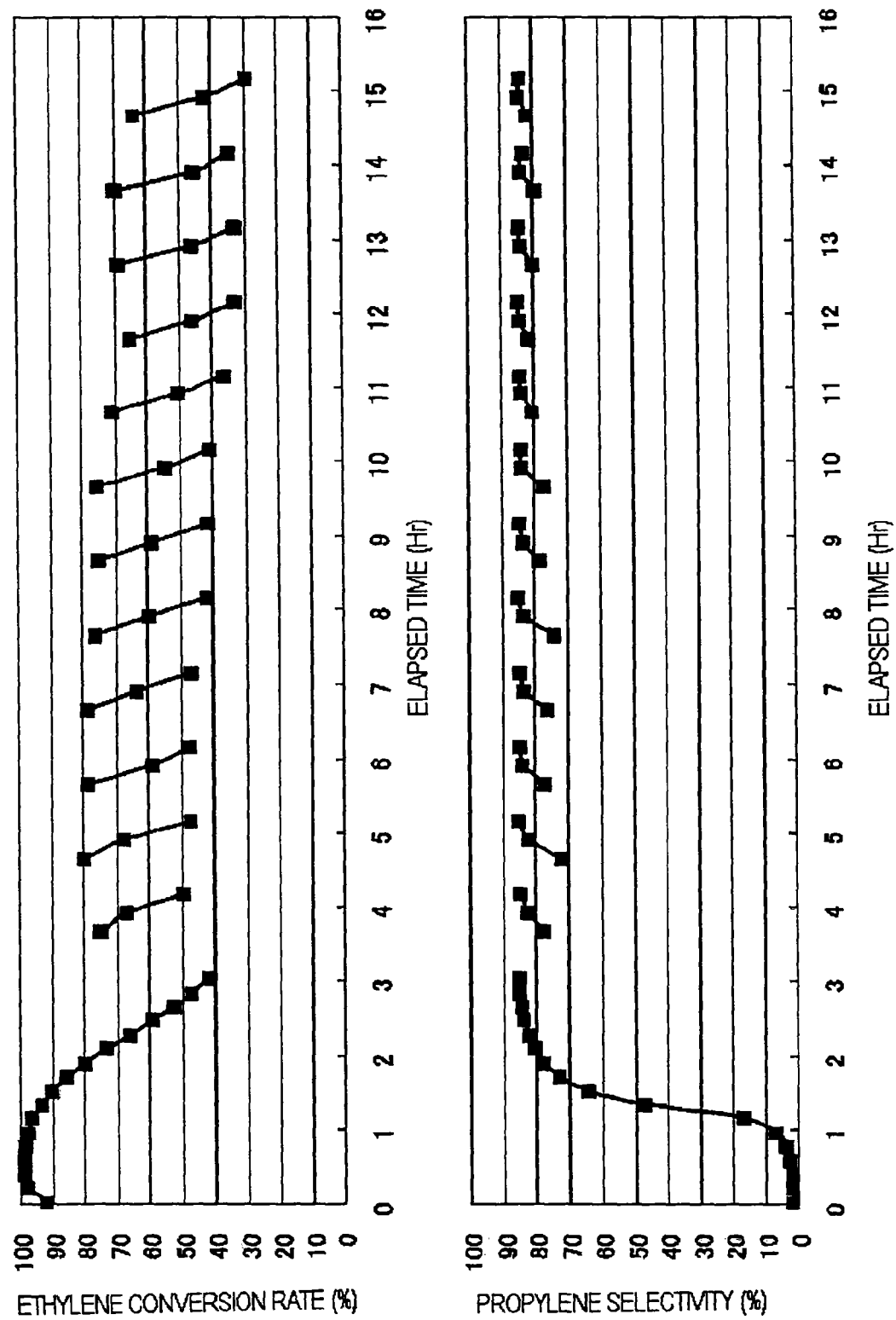
FIG. 2 It is a view showing the temporal change in ethylene conversion and propylene selectivity in repetition of regeneration in Example 3.
Figure 3:
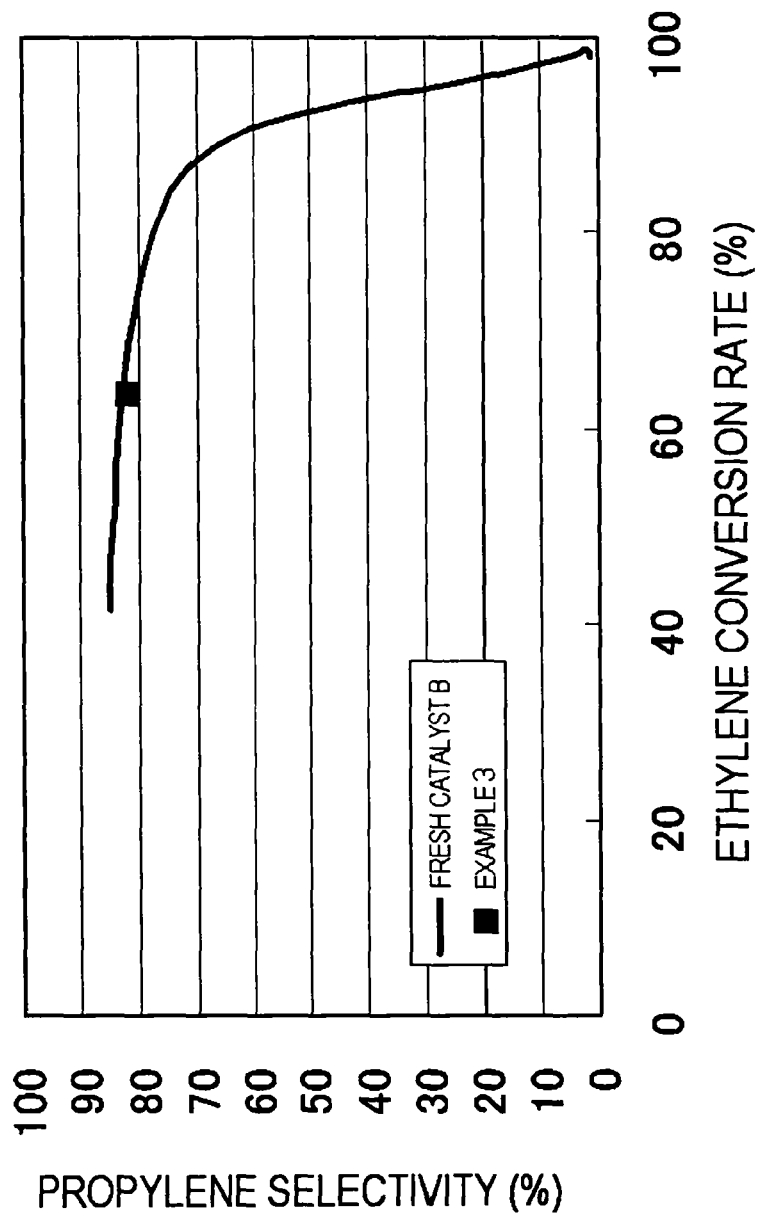
FIG. 3 It is a view showing the relationship between the ethylene conversion and the propylene selectivity of the regenerated catalyst after 12 times regeneration in Example 3.

Using Catalyst B, repetition of a reaction of propylene production from ethylene as a starting material and catalyst regeneration was evaluated in the manner mentioned below.
(1) Primary Reaction For the reaction, used was a fixed-bed flow reactor, in which the quartz reactor tube having an inner diameter of 6 mm was filled with 400 mg of the above zeolite (Catalyst B). Ethylene and nitrogen were fed into the reactor at an ethylene space velocity of 13 mmol/g-cat·h and in a ratio of ethylene of 30% by volume and nitrogen of 70% by volume, and reacted at 400° C. and 0.1 MPa. In 190 minutes after the start of the reaction, the catalyst regeneration was started as described below.
(2) Catalyst Regeneration:

The gas to be fed to the reactor was changed to 100 vol. % hydrogen. In this stage, the hydrogen space velocity was 100 mmol/g-cat·h, and the pressure was 0.10 MPa as the absolute pressure (hydrogen partial pressure of 0.10 MPa). At the same time when the gas was changed to hydrogen, the reactor was heated up to 500° C., taking 10 minutes, and was kept at 500° C. for 5 minutes for catalyst regeneration therein. Afterwards, this was cooled to 400° C., taking 15 minutes, and the following reaction was attained therein.
(3) Reaction:

The gas to be fed to the reactor was changed to ethylene and nitrogen. The concentration, space velocity and pressure of the supply gas were the same as in the above (1). In 30 minutes after the changing into ethylene and nitrogen, the catalyst regeneration of the above (2) was attained, and subsequently, the steps of (1) and (2) were repeated. After 12 cycles of the process of (1) to (3), the temporal change in the ethylene conversion and the propylene selectivity is shown in FIG. 2. The reaction result in the step (3) in the 12th cycle is shown in Table 2, and the relationship between the ethylene conversion and the propylene selectivity is shown in FIG. 3.

As in Table 2, the ethylene conversion before regeneration was 35%; but after regeneration with hydrogen, the ethylene conversion was 64% and the propylene selectivity was 82%. It was found that the propylene selectivity of the hydrogen-regenerated catalyst is nearly at the same level as that of the propylene selectivity of the catalyst before regeneration, and the catalyst is regenerated while maintaining the catalytic capability at the level before regeneration.

As in FIG. 2, it was found that the ethylene conversion in the very primary stage of the reaction in the above (1) is extremely high, but the propylene selectivity is extremely low. In this state, the main product includes paraffins such as propane. From this, it was found that the fresh catalyst or the catalyst after complete removal of coke through regeneration are unsuitable to propylene manufacture.

Example 4

Figure 4:
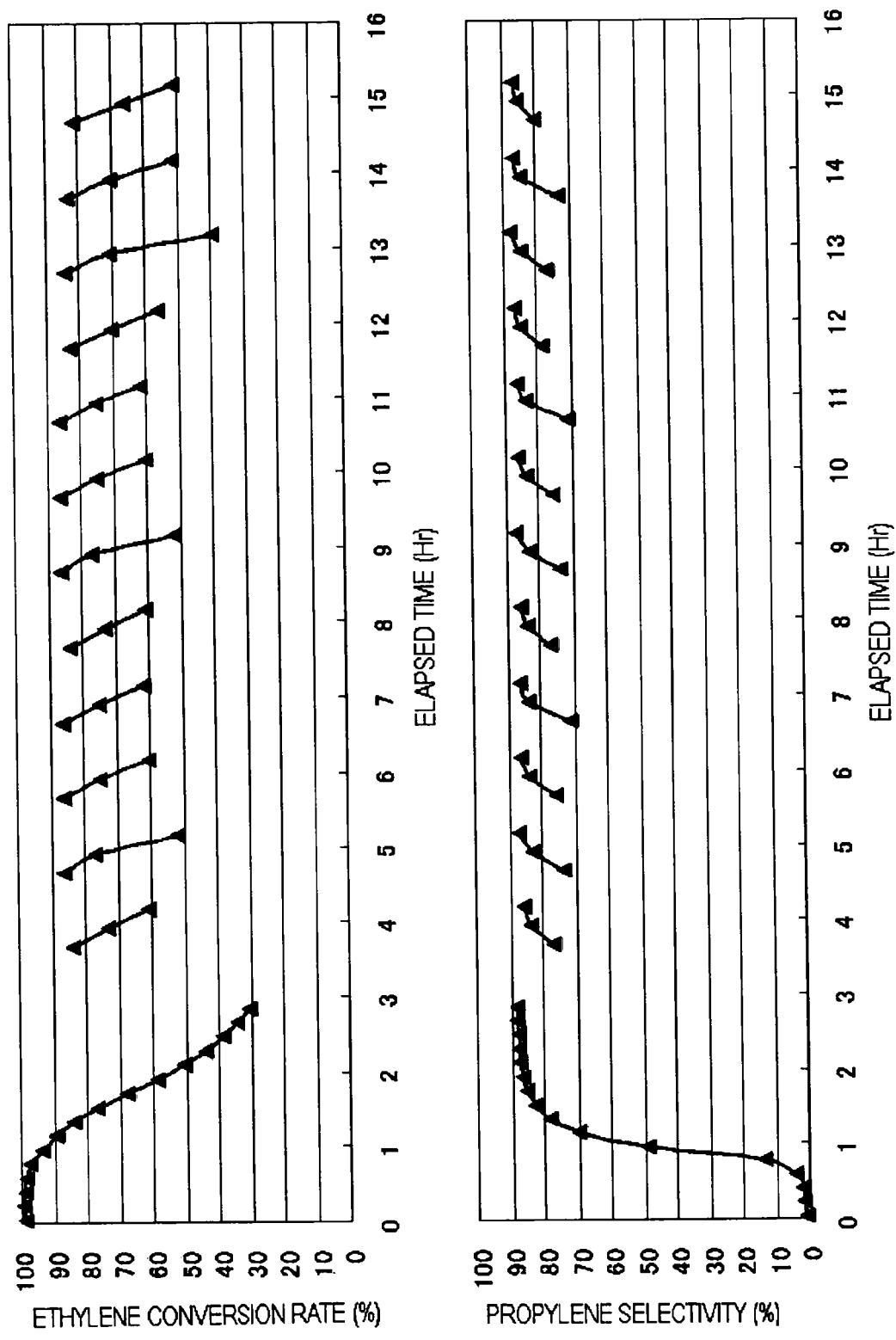
FIG. 4 It is a view showing the temporal change in ethylene conversion and propylene selectivity in repetition of regeneration in Example 4.

The same experiment as in Example 3 was carried out, in which, however, the copper-supported Catalyst C was used in place of the Catalyst B. The process of from (1) to (3) were repeated 12 times, and the temporal change in the ethylene conversion and the propylene selectivity is shown in FIG. 4.

Figure 5:
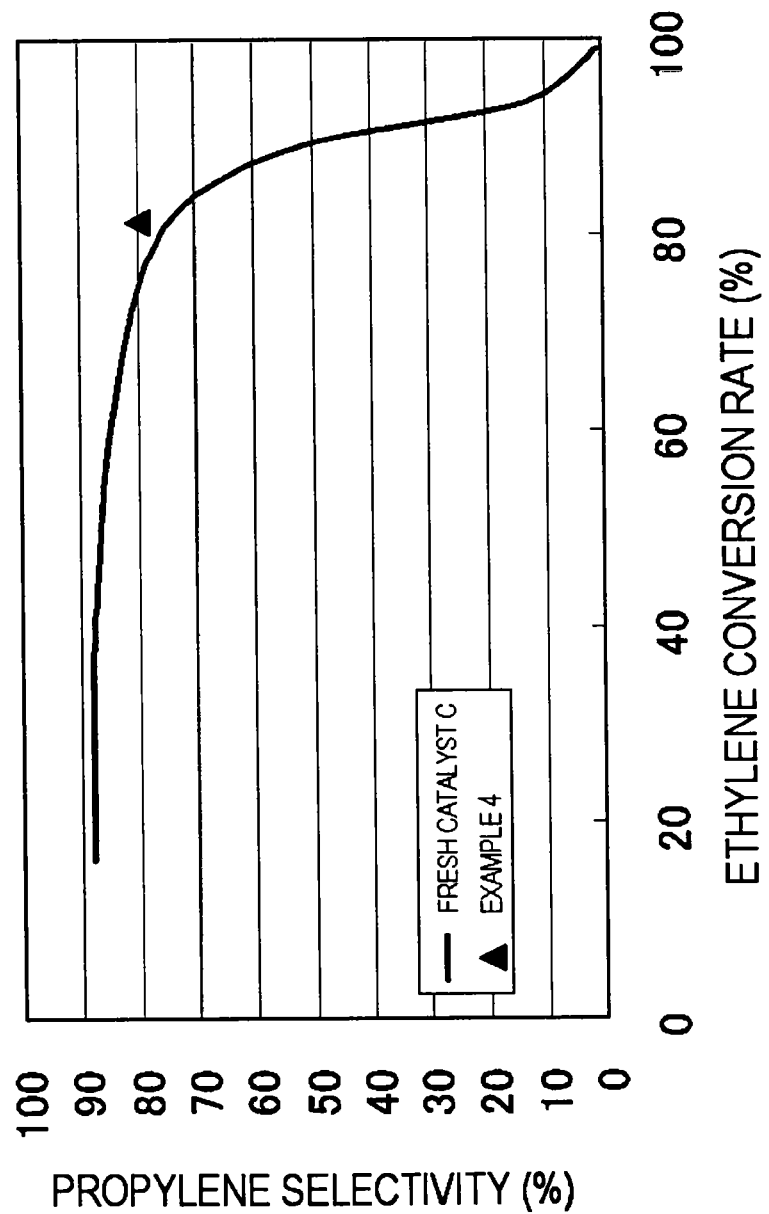
FIG. 5 It is a view showing the relationship between the ethylene conversion and the propylene selectivity of the regenerated catalyst after 12 times regeneration in Example 4.

The reaction result in the step (3) in the 12th cycle is shown in Table 2, and the relationship between the ethylene conversion and the propylene selectivity is shown in FIG. 5.

As in Table 2, the ethylene conversion before regeneration was 51%; but after regeneration with hydrogen, the ethylene conversion was 81% and the propylene selectivity was 80%. From the result, it was found that the propylene selectivity of the hydrogen-regenerated catalyst is nearly at the same level as that of the propylene selectivity of the catalyst before regeneration, and the catalyst is regenerated while maintaining the catalytic capability at the level before regeneration.

This is compared with Example 3, from which it was found that the ethylene conversion of the catalyst before regeneration and after regeneration is higher by 15% or more. This may be presumed because the copper which the catalyst supports would promote the hydrogenolysis of coke deposition to the catalyst thereby increasing the regeneration speed.

TABLE 2

| | Example 3 | Example 4 |
|---|---|---|
| Catalyst | B | C |
| Regeneration Gas Pressure (MPa) | 0.1 | 0.1 |
| Hydrogen Partial Pressure (MPa) | 0.1 | 0.1 |
| Reaction Temperature | 400 | 400 |
| Reaction Time (min) | 30 | 30 |
| Regeneration Temperature | 500 | 500 |
| Regeneration Time (min) | 5 | 5 |
| Hydrogen Space Velocity ($hr^{-1}$) | 100 | 100 |
| Ethylene Conversion before regeneration (%) | 35 | 51 |
| Ethylene Conversion after regeneration (%) | 64 | 81 |
| Propylene Selectivity (%) | 82 | 80 |
| Ethane Selectivity (%) | 6 | 5 |
| Propane Selectivity (%) | 3 | 6 |
| C4 Selectivity (%) | 4 | 4 |
| C5+ Selectivity (%) | 4 | 4 |
| Difference in Propylene Selectivity* | −1 | 5 |

*Difference in propylene selectivity between fresh catalyst and regenerated catalyst at the same conversion.

Example 5

After the experiment of Example 3, an additional experiment in which the condition of the above (2) and (3) was changed to the following, was performed.
(2) Catalyst Regeneration:

The gas to be fed to the reactor was changed to 100 vol. % hydrogen. In this stage, the hydrogen space velocity was 100 mmol/g-cat·h, and the pressure was 0.10 MPa as the absolute pressure (hydrogen partial pressure of 0.10 MPa). At the same time when the gas was changed to hydrogen, the reactor was heated up to 480° C., taking 10 minutes, and was kept at 480° C. for 5 minutes for catalyst regeneration therein. Afterwards, this was cooled to 350° C., taking 15 minutes, and the reaction of the step (3) was attained therein.

(3) Reaction:

The gas to be fed to the reactor was changed to ethylene and nitrogen. In this state, the gas was fed to the reactor at an ethylene space velocity of 13 mmol/g-cat·h and in a ratio of ethylene of 30% by volume and nitrogen of 70% by volume, and the reaction was attained at 350° C. and 0.10 MPa. In 20 minutes after changing to ethylene and nitrogen, the catalyst regeneration of the step (2) was attained, and subsequently, the steps (2) and (3) were repeated.

Figure 6:
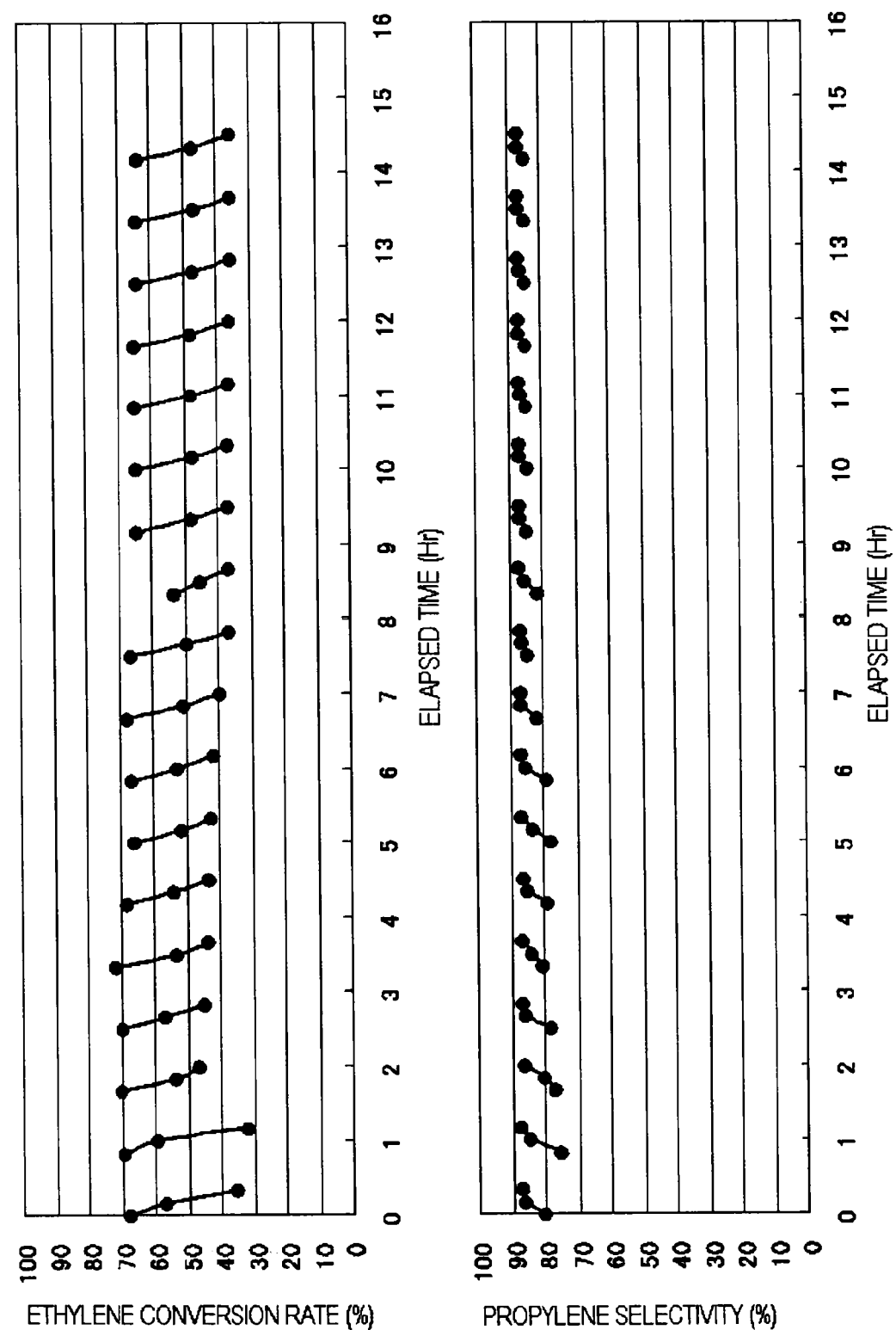
FIG. 6 It is a view showing the temporal change in ethylene conversion and propylene selectivity in repetition of regeneration in Example 5.

After 18 cycles of the process, the temporal change in the ethylene conversion and the propylene selectivity is shown in FIG. 6. The reaction result in the step (3) in the 18th cycle is shown in Table 3.

As in Table 3, the ethylene conversion before regeneration was 36%; but after regeneration with hydrogen, the ethylene conversion was 63% and the propylene selectivity was 85%. From the result, it was found that the propylene selectivity of the hydrogen-regenerated catalyst is extremely high.

Example 6

Figure 7:
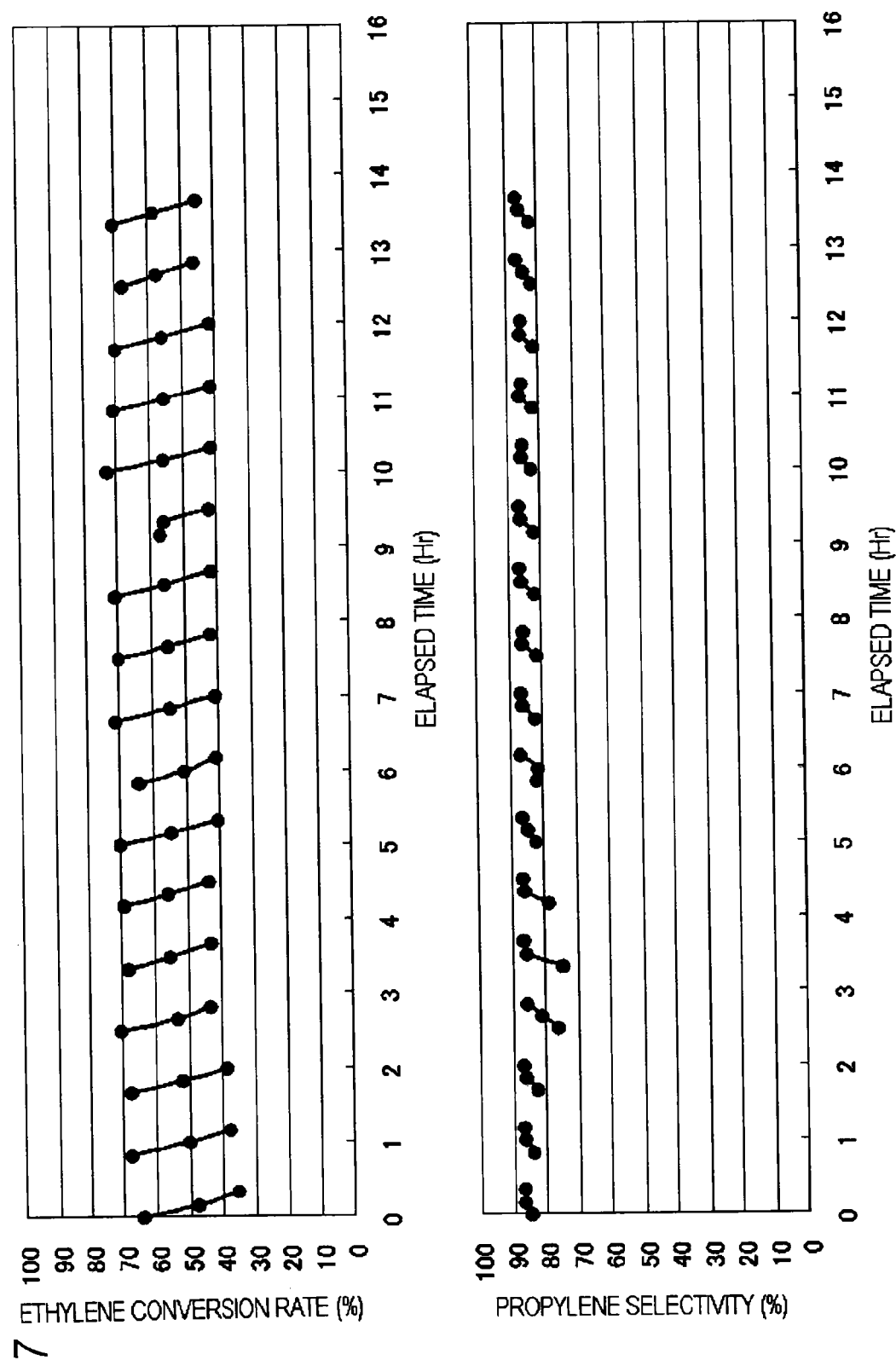
FIG. 7 It is a view showing the temporal change in ethylene conversion and propylene selectivity in repetition of regeneration in Example 6.

After the experiment of Example 5, an additional experiment under the same condition as in Example 5, in which, however, the temperature in the step (2) was changed from 480° C. to 490° C., was performed. After 17 cycles of the process of the above (2) and (3), the temporal change in the ethylene conversion and the propylene selectivity is shown in FIG. 7. The reaction result in the step (3) in the 17th cycle is shown in Table 3.

As in Table 3, the ethylene conversion before regeneration was 46%; but after regeneration with hydrogen, the ethylene conversion was 70% and the propylene selectivity was 82%. From the result, it was found that the propylene selectivity of the hydrogen-regenerated catalyst is extremely high.

Example 7

After the experiment of Example 6, an additional experiment under the same condition as in Example 6, in which, however, the temperature in the step (2) of Example 5 was changed from 490° C. to 500° C., was performed.

Figure 8:
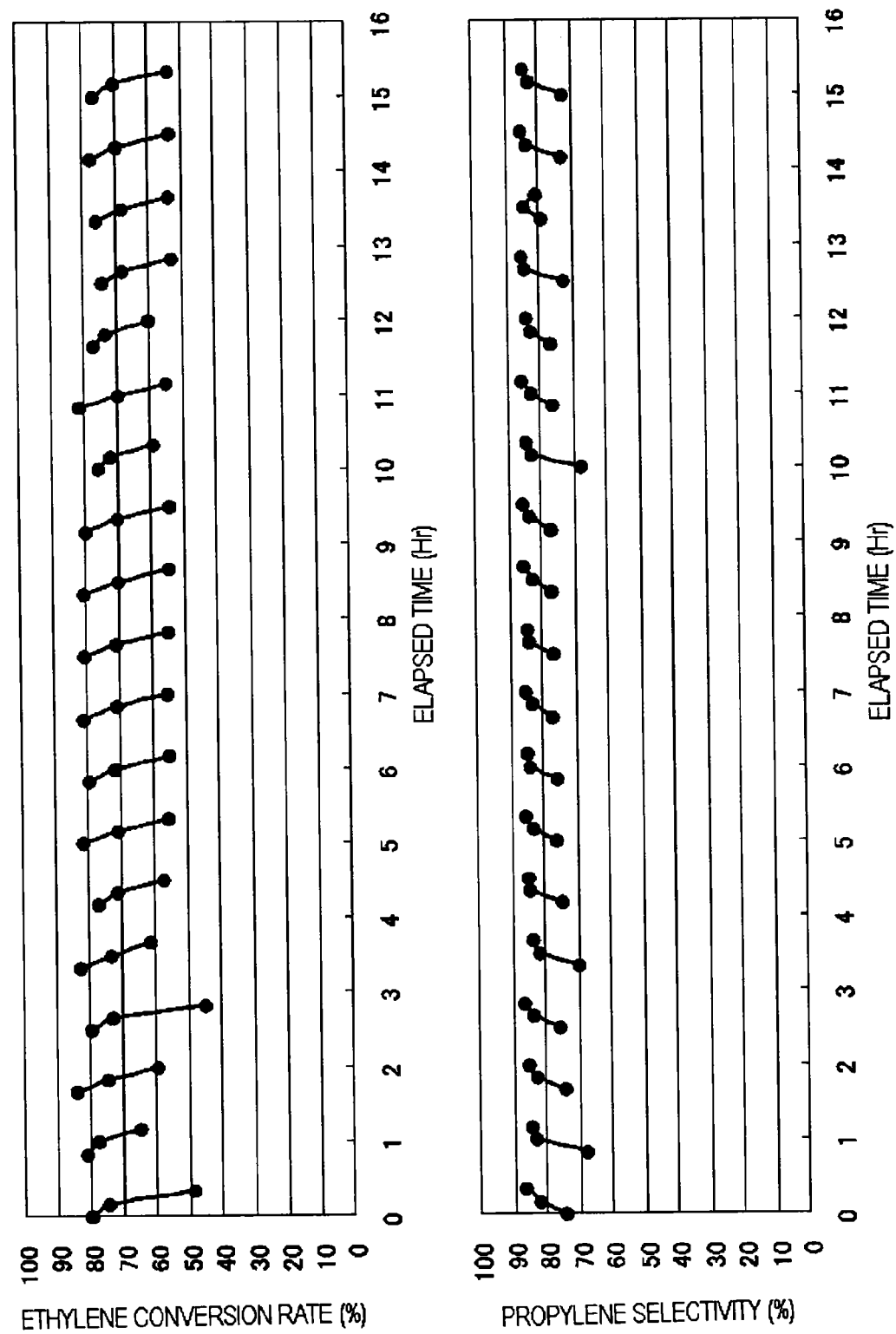
FIG. 8 It is a view showing the temporal change in ethylene conversion and propylene selectivity in repetition of regeneration in Example 7.

After 19 cycles of the process of (2) and (3) of Example 5, the temporal change in the ethylene conversion and the propylene selectivity is shown in FIG. 8. The reaction result in the step (3) of Example 5 in the 19th cycle is shown in Table 3.

As in Table 3, the ethylene conversion before regeneration was 53%; but after regeneration with hydrogen, the ethylene conversion was 76% and the propylene selectivity was 72%. From the result, it was found that the propylene selectivity of the hydrogen-regenerated catalyst is extremely high.

Examples 5 to 7 were compared with each other, which revealed that, when the regeneration temperature is elevated, then the ethylene conversion can be kept at a high level. This may be presumed because the regeneration speed would be increased.

On the other hand, it was also found that, when the ethylene conversion of the catalyst after regeneration is too high, then the propylene selectivity thereof tends to lower. From this, it was found that in an actual process, the system is preferably so driven that the ethylene conversion of the regenerated catalyst could be from about 50 to 90%.

Example 8

Figure 9:
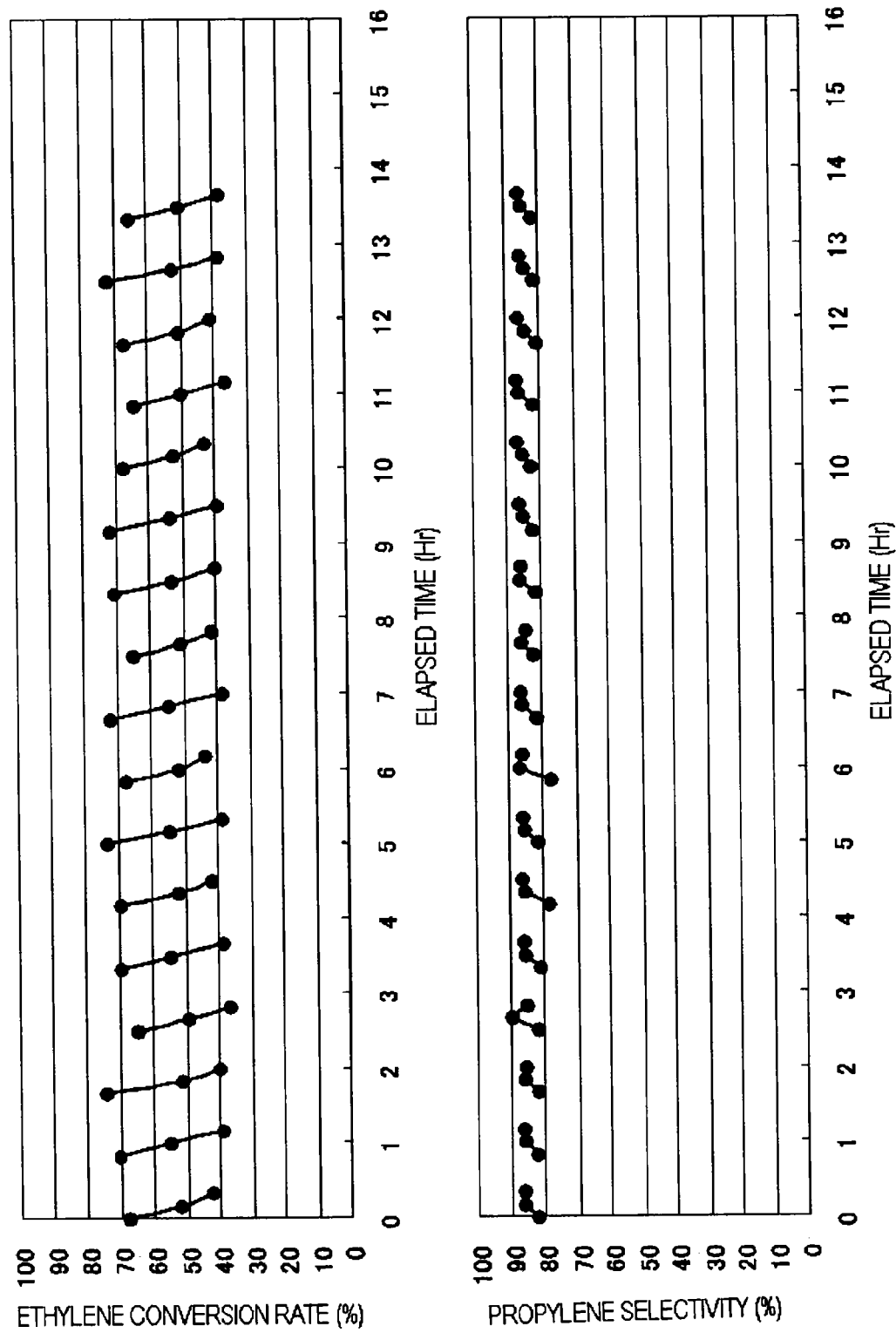
FIG. 9 It is a view showing the temporal change in ethylene conversion and propylene selectivity in repetition of regeneration in Example 8.

After the experiment of Example 7, an additional experiment under the same condition as in Example 7, in which, however, the hydrogen space velocity in the step (2) of Example 5 was changed from 100 to 44 mmol/g-cat·h, was performed. After 17 cycles of the process of (2) and (3), the temporal change in the ethylene conversion and the propylene selectivity is shown in FIG. 9.

The result in the step (3) of Example 5 in the 17th cycle is shown in Table 3. As in Table 3, the ethylene conversion before regeneration was 38%, but the ethylene conversion after regeneration with hydrogen was 65% and the propylene selectivity was 83%. It was found that the propylene selectivity of the hydrogen-regenerated catalyst is extremely high.

This is compared with Example 7, from which it was found that, when the hydrogen space velocity is higher, then the ethylene conversion can be kept at a high level. This may be presumed because, when the space velocity is higher, then the concentration of the hydrocarbon to be formed in regeneration could be lower and the redeposition thereof on the catalyst bed could be retarded.

On the other hand, when the hydrogen space velocity is too high, then the amount of hydrogen to be used increases, and this may be disadvantageous from the viewpoint of economical aspect.

TABLE 3

| | Example 3 | Example 5 | Example 6 | Example 7 | Example 8 |
|---|---|---|---|---|---|
| Catalyst | B | B | B | B | B |
| Reaction Temperature | 400 | 350 | 350 | 350 | 350 |
| Reaction Time (min) | 30 | 20 | 20 | 20 | 20 |
| Regeneration Temperature | 500 | 480 | 490 | 500 | 500 |
| Regeneration Time (min) | 5 | 5 | 5 | 5 | 5 |
| Hydrogen Space Velocity ($hr^{-1}$) | 100 | 100 | 100 | 100 | 44 |
| Ethylene Conversion before regeneration (%) | 35 | 36 | 46 | 53 | 38 |
| Ethylene Conversion after regeneration (%) | 64 | 63 | 70 | 76 | 65 |
| Propylene Selectivity (%) | 82 | 85 | 82 | 72 | 83 |
| Ethane Selectivity (%) | 6 | 4 | 5 | 7 | 5 |
| Propane Selectivity (%) | 3 | 3 | 4 | 9 | 4 |
| C4 Selectivity (%) | 4 | 4 | 4 | 5 | 3 |
| C5+ Selectivity (%) | 4 | 4 | 4 | 4 | 4 |

Example 9

(1) Reaction

The reaction was performed in the same as in Example 1, in which, however, the Catalyst D was used, the reaction time was 3 hours and 10 minutes and the catalyst amount was 200 mg. In the case where the fresh catalyst was used, the ethylene conversion at the end of the reaction was around 26%. Using the catalyst after the reaction (this is herein referred to as "degraded Catalyst D1"), the catalyst was regenerated and propylene was produced. The relationship between the ethylene conversion and the propylene selectivity in use of the fresh catalyst is shown by the solid line in FIG. 10.

(2) Catalyst Regeneration and Propylene Production 100 vol. % hydrogen gas was fed to the degraded Catalyst D1 (ethylene conversion: 26%) at a hydrogen space velocity of 104 mmol/g·cat·h; and at 500° C. and under an absolute pressure of 0.10 MPa (hydrogen partial pressure of 0.10 MPa), the catalyst was regenerated for 5 minutes. The oxygen content of the regeneration gas was 0% by volume (oxygen partial pressure of 0.00 MPa).

Figure 10:
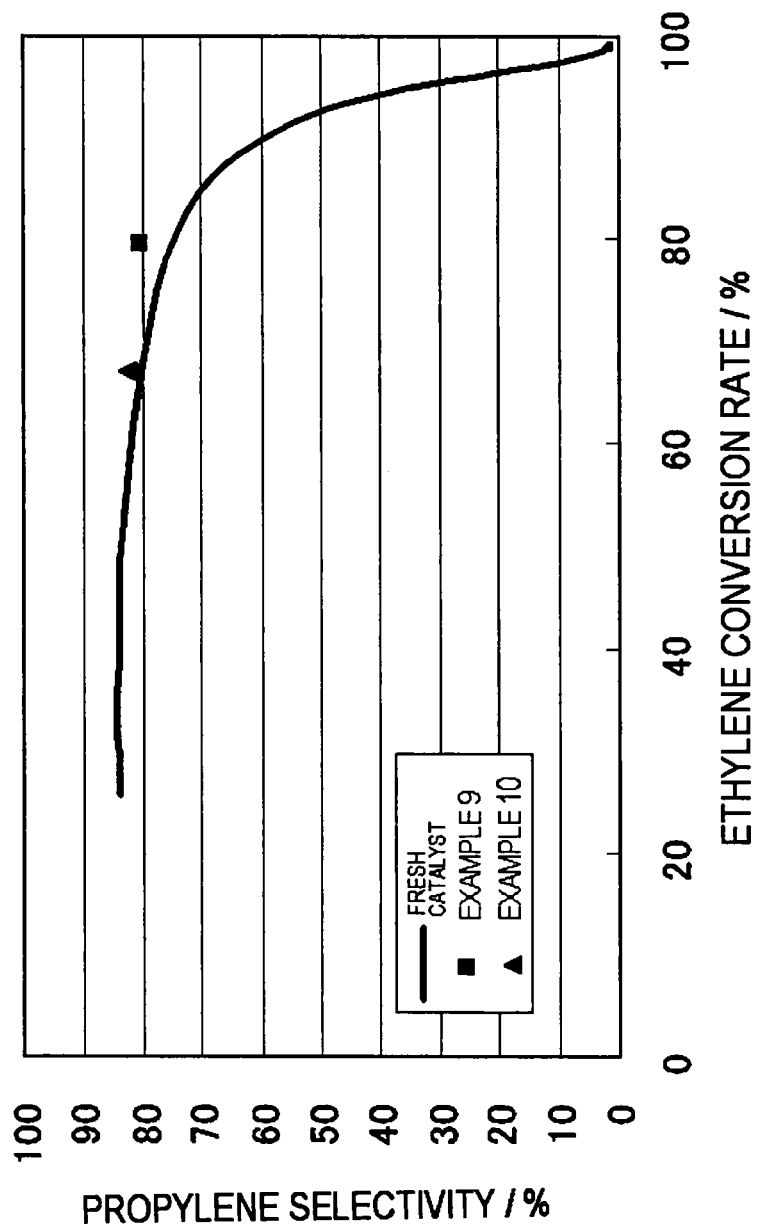
FIG. 10 It is a view showing the relationship between the ethylene conversion and the propylene selectivity of the catalyst in Example 9.

After the regeneration, the reaction was again performed under the same condition as above, and immediately after the start of the reaction, the reaction result was confirmed. Table 1 shows the reaction result; and FIG. 10 shows the relationship between the ethylene conversion and the propylene selectivity.

As in Table 1, the ethylene conversion before regeneration was 26%; but after regeneration with hydrogen, the ethylene conversion was 80% and the propylene selectivity was 80%. The propylene selectivity of the hydrogen-regenerated catalyst was nearly at the same level as that of the propylene selectivity of the temporally-degraded catalyst from the fresh catalyst when the two were compared with each other at the same conversion level. From the result, it was found that even the catalyst having a different aluminium content can be activated and can be regenerated to have an increased propylene selectivity while maintaining the catalytic capability at the level before regeneration.

Example 10

(1) Reaction

The reaction was performed in the same as in Example 1, in which, however, the Catalyst D was used, the reaction time was 2 hours and 30 minutes and the catalyst amount was 200 mg. In the case where the fresh catalyst was used, the ethylene conversion at the end of the reaction was around 36%. Using the catalyst after the reaction (this is herein referred to as "degraded Catalyst D2"), the catalyst was regenerated and propylene was produced. The relationship between the ethylene conversion and the propylene selectivity in use of the fresh catalyst is shown by the solid line in FIG. 10.

(2) Catalyst Regeneration and Propylene Production

A regeneration gas of 20 vol. % hydrogen and 80 vol. % nitrogen was fed to the degraded Catalyst D2 (ethylene conversion: 36%) at a hydrogen space velocity of 21 mmol/g·cat·h; and at 500° C. and under an absolute pressure of 0.10 MPa (hydrogen partial pressure of 0.02 MPa), the catalyst was regenerated for 5 minutes. The oxygen content of the regeneration gas was 0% by volume (oxygen partial pressure of 0.00 MPa).

After the regeneration, the reaction was again performed under the same condition as above, and immediately after the start of the reaction, the reaction result was confirmed. Table 1 shows the reaction result; and FIG. 10 shows the relationship between the ethylene conversion and the propylene selectivity.

As in Table 1, the ethylene conversion before regeneration was 36%; but after regeneration with hydrogen, the ethylene conversion was 67% and the propylene selectivity was 82%. The propylene selectivity of the hydrogen-regenerated catalyst was nearly at the same level as that of the propylene selectivity of the temporally-degraded catalyst from the fresh catalyst when the two were compared with each other at the same conversion level. From the result, it was found that the catalyst can be activated even by hydrogen regeneration under a reduced partial hydrogen pressure, and can be regenerated while maintaining the catalytic capability at the level before regeneration.

While the invention has been described in detail and with reference to specific embodiments thereof, it will be apparent to one skilled in the art that various changes and modifications can be made therein without departing from the spirit and scope thereof. The present application is based on basic applications of a Japanese patent application No. 2009-186269 filed on Aug. 11, 2009 and a Japanese patent application No. 2009-211826 filed on Sep. 14, 2009, the entire contents thereof being hereby incorporated.

The invention claimed is:

1. A method for manufacturing a catalyst, which comprises regenerating a catalyst comprising an aluminosilicate zeolite having a CHA structure as an active ingredient and having an ethylene conversion lowered through a reaction of producing propylene by bringing into contact with ethylene in a vapor phase, by bringing the catalyst into contact with a gas which does not comprise oxygen and comprises hydrogen having a hydrogen partial pressure of 0.01 MPa or more as an absolute pressure thereof.

2. The method for manufacturing a catalyst according to claim 1, wherein a temperature at which the catalyst is regenerated is 300° C. or more and 750° C. or less.

3. The method for manufacturing a catalyst according to claim 1, wherein the catalyst is regenerated until the ethylene conversion reaches the range from 50 to 90% and a propylene selectivity reaches 40% or more, when the regenerated catalyst is brought into contact with ethylene in a vapor phase to produce propylene at the same temperature, under the same pressure and at the same space velocity as those in the reaction to produce propylene.

4. The method for manufacturing a catalyst according to claim 1, wherein the catalyst is a metal-supported zeolite.

5. The method for manufacturing a catalyst according to claim 1, wherein the zeolite has a mean pore size of less than 0.6 nm.

6. A method for manufacturing propylene, comprising bringing a starting material comprising ethylene into contact with the catalyst manufactured in the method according to claim 1 in a reactor.

7. The method for manufacturing propylene according to claim 6, wherein a device for regenerating a catalyst is attached to the reactor, the catalyst taken out of the reactor is transferred to the device, and the regenerated catalyst is returned back to the reactor to perform the reaction.

* * * * *